US009598375B2

(12) United States Patent
Jones et al.

(10) Patent No.: US 9,598,375 B2
(45) Date of Patent: Mar. 21, 2017

(54) SUBSTITUTED IMIDAZOLE DERIVATIVES AND METHODS OF USE THEREOF

(71) Applicant: vTv Therapeutics LLC, High Point, NC (US)

(72) Inventors: David Jones, Milford, OH (US); Raju Bore Gowda, Oak Ridge, NC (US); Rongyuan Xie, Greensboro, NC (US)

(73) Assignee: vTv Therapeutics LLC, High Point, NC (US)

( * ) Notice: Subject to any disclaimer, the term of this patent is extended or adjusted under 35 U.S.C. 154(b) by 241 days.

(21) Appl. No.: 14/049,261

(22) Filed: Oct. 9, 2013

(65) Prior Publication Data

US 2014/0039025 A1 Feb. 6, 2014

Related U.S. Application Data

(62) Division of application No. 12/888,660, filed on Sep. 23, 2010, now Pat. No. 8,580,833.

(60) Provisional application No. 61/247,206, filed on Sep. 30, 2009.

(51) Int. Cl.
*C07D 233/64* (2006.01)
*C07D 233/60* (2006.01)

(52) U.S. Cl.
CPC ......... *C07D 233/64* (2013.01); *C07D 233/60* (2013.01)

(58) Field of Classification Search
CPC .................................. C07D 233/64
See application file for complete search history.

(56) References Cited

U.S. PATENT DOCUMENTS

| | | | |
|---|---|---|---|
| 3,255,202 A | 6/1966 | Johnson | |
| 3,708,598 A | 1/1973 | Griot | |
| 3,951,968 A | 4/1976 | Fauran et al. | |
| 4,024,271 A | 5/1977 | Durant et al. | |
| 4,032,522 A | 6/1977 | Baldwin et al. | |
| 4,166,452 A | 9/1979 | Generales, Jr. | |
| 4,265,874 A | 5/1981 | Bonsen et al. | |
| 4,356,108 A | 10/1982 | Schwab et al. | |
| 4,873,313 A | 10/1989 | Crawford et al. | |
| 4,933,422 A | 6/1990 | Hammer | |
| 4,963,539 A | 10/1990 | Delaney | |
| 5,011,849 A | 4/1991 | Gassner et al. | |
| 5,153,226 A | 10/1992 | Chucholowski et al. | |
| 5,166,214 A | 11/1992 | Billheimer et al. | |
| 5,179,210 A | 1/1993 | Ebel | |
| 5,192,785 A | 3/1993 | Lo et al. | |
| 5,202,424 A | 4/1993 | Vlassara et al. | |
| 5,318,984 A | 6/1994 | Billheimer et al. | |
| 5,358,960 A | 10/1994 | Ulrich et al. | |
| 5,500,436 A | 3/1996 | Schoenafinger et al. | |
| 5,523,317 A | 6/1996 | Masaki et al. | |
| 5,585,344 A | 12/1996 | Vlassara et al. | |
| 5,589,496 A | 12/1996 | Hamanaka et al. | |
| 5,663,186 A | 9/1997 | Nelson et al. | |
| 5,688,653 A | 11/1997 | Ulrich et al. | |
| 5,703,092 A | 12/1997 | Xue et al. | |
| 5,795,907 A | 8/1998 | Kalindjian et al. | |
| 5,817,626 A | 10/1998 | Findeis et al. | |
| 5,817,823 A | 10/1998 | Hong et al. | |
| 5,840,294 A | 11/1998 | Kisilevsky et al. | |
| 5,864,018 A | 1/1999 | Morser et al. | |
| 5,922,770 A | 7/1999 | Peschke et al. | |
| 5,939,526 A | 8/1999 | Gaugler et al. | |
| 5,962,500 A | 10/1999 | Eide et al. | |
| 5,962,535 A | 10/1999 | Miyamoto et al. | |
| 6,034,250 A | 3/2000 | Goldstein et al. | |
| 6,100,098 A | 8/2000 | Newkirk | |
| 6,197,791 B1 | 3/2001 | Venkatesan et al. | |
| 6,201,002 B1 | 3/2001 | Beere et al. | |
| 6,221,667 B1 | 4/2001 | Reiner et al. | |
| 6,265,351 B1 | 7/2001 | Porta et al. | |
| 6,268,479 B1 | 7/2001 | Stern et al. | |
| 6,274,615 B1 | 8/2001 | Pappolla et al. | |
| 6,277,853 B1 | 8/2001 | Perez et al. | |
| 6,300,356 B1 | 10/2001 | Segal et al. | |
| 6,316,474 B1 | 11/2001 | McCauley et al. | |

(Continued)

FOREIGN PATENT DOCUMENTS

EP 0584588 A1 3/1994
EP 0586806 A1 3/1994

(Continued)

OTHER PUBLICATIONS

Albericio et al., "Coupling Reagents and Activation," Methods in Enzymology 289:104-126 (1997).

(Continued)

*Primary Examiner* — Samira Jean-Louis
(74) *Attorney, Agent, or Firm* — Samuel B. Rollins

(57) ABSTRACT

The present invention provides imidazole derivatives of Formula (I) and pharmaceutically acceptable salts thereof.

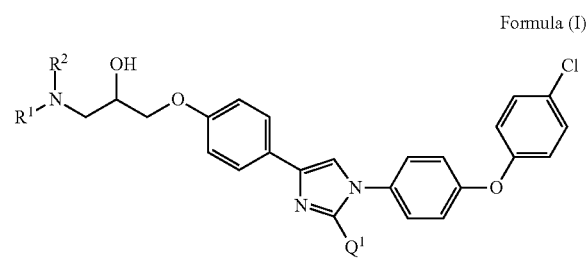

Formula (I)

and their use in the treatment of diseases such as Alzheimer's Disease.

9 Claims, No Drawings

(56) References Cited

U.S. PATENT DOCUMENTS

| | | | |
|---|---|---|---|
| 6,323,218 B1 | 11/2001 | Bush et al. |
| 6,353,009 B1 | 3/2002 | Fujiwara et al. |
| 6,416,733 B1 | 7/2002 | Barrett et al. |
| 6,441,023 B1 | 8/2002 | Venkatesan et al. |
| 6,441,049 B2 | 8/2002 | Reitz et al. |
| 6,441,064 B1 | 8/2002 | Shah et al. |
| 6,472,145 B2 | 10/2002 | Reiner et al. |
| 6,538,013 B2 | 3/2003 | Goebel et al. |
| 6,541,639 B2 | 4/2003 | Zhou et al. |
| 6,613,801 B2 | 9/2003 | Mjalli et al. |
| 6,673,810 B2 | 1/2004 | Lam et al. |
| 6,673,927 B2 | 1/2004 | Gordon et al. |
| 6,677,299 B2 | 1/2004 | Stern et al. |
| 6,730,796 B2 | 5/2004 | Cheng et al. |
| 6,825,164 B1 | 11/2004 | Stern et al. |
| 6,919,338 B2 | 7/2005 | Mortlock et al. |
| 7,067,554 B2 | 6/2006 | Mjalli et al. |
| 7,087,632 B2 | 8/2006 | Mjalli et al. |
| 7,329,684 B2 | 2/2008 | Mjalli et al. |
| 7,361,678 B2 | 4/2008 | Mjalli et al. |
| 7,421,177 B2 | 9/2008 | Schmidt et al. |
| 7,423,177 B2 | 9/2008 | Mjalli et al. |
| 7,714,013 B2 | 5/2010 | Mjalli et al. |
| 7,737,285 B2 | 6/2010 | Mjalli et al. |
| 7,776,919 B2 | 8/2010 | Mjalli et al. |
| 7,884,219 B2 | 2/2011 | Hari |
| 8,372,988 B2 | 2/2013 | Hari |
| 8,580,833 B2 | 11/2013 | Jones et al. |
| 2001/0039256 A1 | 11/2001 | Stern et al. |
| 2002/0006957 A1 | 1/2002 | Mjalli et al. |
| 2002/0116725 A1 | 8/2002 | Stern et al. |
| 2002/0122799 A1 | 9/2002 | Stern et al. |
| 2002/0193432 A1 | 12/2002 | Mjalli et al. |
| 2003/0032663 A1 | 2/2003 | Mjalli et al. |
| 2003/0207896 A1 | 11/2003 | Konno et al. |
| 2003/0236282 A1 | 12/2003 | Hurnaus et al. |
| 2004/0063770 A1 | 4/2004 | Ahn et al. |
| 2004/0082542 A1 | 4/2004 | Mjalli et al. |
| 2004/0097407 A1 | 5/2004 | Mjalli et al. |
| 2004/0127692 A1 | 7/2004 | David et al. |
| 2005/0026811 A1 | 2/2005 | Mjalli et al. |
| 2006/0020042 A1 | 1/2006 | McDonald et al. |
| 2006/0247253 A1 | 11/2006 | Leban et al. |
| 2007/0021386 A1 | 1/2007 | Mjalli et al. |
| 2007/0135437 A1 | 6/2007 | Benjamin et al. |
| 2009/0035302 A1 | 2/2009 | Mjalli et al. |
| 2010/0048726 A1 | 2/2010 | McDonald et al. |
| 2010/0256119 A1 | 10/2010 | Mjalli et al. |
| 2012/0088778 A1 | 4/2012 | Mjalli et al. |
| 2014/0039025 A1 | 2/2014 | Jones et al. |

FOREIGN PATENT DOCUMENTS

| | | |
|---|---|---|
| EP | 0633026 A1 | 1/1995 |
| EP | 0707000 A1 | 4/1996 |
| EP | 1139990 | 10/2001 |
| FR | 1476560 | 4/1967 |
| FR | 2773800 A1 | 7/1999 |
| GB | 2005674 A | 4/1979 |
| JP | 60-080656 A | 3/1994 |
| JP | 90-040651 A | 2/1997 |
| JP | 2003-012690 A | 1/2003 |
| JP | 2003-040888 A | 2/2003 |
| JP | 2003-313170 A | 11/2003 |
| JP | 2003-313172 A | 11/2003 |
| JP | 2004-221557 A | 8/2004 |
| WF | WO 00/66102 A2 | 11/2000 |
| WO | WO 93/09100 A1 | 5/1993 |
| WO | WO 95/01340 A1 | 1/1995 |
| WO | WO 95/02591 A1 | 1/1995 |
| WO | WO 95/09838 A1 | 4/1995 |
| WO | WO 95/30647 A1 | 11/1995 |
| WO | WO 95/35279 A1 | 12/1995 |
| WO | WO 96/32385 A1 | 10/1996 |
| WO | WO 97/22618 A1 | 6/1997 |
| WO | WO 97/26913 A1 | 7/1997 |
| WO | WO 97/39121 A1 | 10/1997 |
| WO | WO 97/39125 A1 | 10/1997 |
| WO | WO 98/22138 A1 | 5/1998 |
| WO | WO 98/27108 A2 | 6/1998 |
| WO | WO 98/33492 A1 | 8/1998 |
| WO | WO 98/35945 A1 | 8/1998 |
| WO | WO 98/37877 A1 | 9/1998 |
| WO | WO 99/07402 A1 | 2/1999 |
| WO | WO 99/16755 A1 | 4/1999 |
| WO | WO 99/18987 A1 | 4/1999 |
| WO | WO 99/25690 A2 | 5/1999 |
| WO | WO 99/50230 A1 | 10/1999 |
| WO | WO 99/54485 A1 | 10/1999 |
| WO | WO 00/19994 A1 | 4/2000 |
| WO | WO 00/20458 A1 | 4/2000 |
| WO | WO 00/20621 A1 | 4/2000 |
| WO | WO 00/38635 A1 | 7/2000 |
| WO | WO 01/12598 A2 | 2/2001 |
| WO | WO 01/32604 A1 | 5/2001 |
| WO | WO 01/92210 A1 | 12/2001 |
| WO | WO 02/069965 A1 | 9/2002 |
| WO | WO 02/070473 A2 | 9/2002 |
| WO | WO 03/024937 A1 | 3/2003 |
| WO | WO 03/053922 A2 | 7/2003 |
| WO | WO 03/075921 A2 | 9/2003 |
| WO | WO 03/086390 A1 | 10/2003 |
| WO | WO 03/075921 A3 | 12/2003 |
| WO | WO 2004/035061 A1 | 4/2004 |
| WO | WO 2004/046141 A | 6/2004 |
| WO | WO 2004/087653 A2 | 10/2004 |
| WO | WO 2004/110350 A2 | 12/2004 |
| WO | WO 2005/000295 A1 | 1/2005 |
| WO | WO 2005/019185 A1 | 3/2005 |
| WO | WO 2006/124897 A2 | 11/2006 |
| WO | WO 2008/067121 A2 | 6/2008 |
| WO | WO 2008/153957 A1 | 12/2008 |
| WO | WO 2010/126745 A1 | 11/2010 |
| WO | WO 2011/103091 A1 | 8/2011 |

OTHER PUBLICATIONS

Barton, "Protection of N—H Bonds and NR3," Protective Groups in Organic Chemistry, McOmie, Ed., pp. 43-93 (1973).

Behl et al., "Amyloid beta peptide induces necrosis rather than apoptosis," Brain Research 645:253-264 (1994).

Behl, "Hydrogen Peroxide Mediates Amyloid beta Protein Toxicity," Cell 77:817-827 (1994).

Berge et al., "Pharmaceutical Salts," Journal of Pharmaceutical Sciences 66(1):1-19 (1977).

Bierhaus et al., "Advanced Glycation End Product (AGE)-Mediated Induction of Tissue Factor in Cultured Endothelial Cells Is Dependent on RAGE," Circulation 96:2262-2271 (1997).

Blacker et al., "Reliability and Validity of NINCDS-ADRDA Criteria for Alzheimer's Disease," Arch. Neurol. 51:1198-1204 (1994).

Bonnardel-Phu et al., "Acute Modulation of Albumin Microvascular Leakage by Adanced Glycation End Products in Microcirculation of Diabetic Rats In Vivo," Diabetes 48:2052-2058 (1999).

Buttke et al., "Synthesis, Structure, and Photophysical Properties of Polyarylated Imidazoles and Oxazoles," J. prakt. Chem. 339:721-728 (1997).

Chartier-Harlin et al., "Early-onset Alzheimer's disease caused by mutations at codon 717 of the beta-amyloid precursor protein gene," Nature 353:844-846 (1991).

Checler, "Processing of the beta-Amyloid Precursor Protein and Its Regulation in Alzheimer's Disease," Journal of Neurochemistry 65(4):1431-1444 (1995).

Chitaley et al., "Antagonism of Rho-kinase stimulates rat penile erection via a erection via a nitric oxide-independent pathway," Nature Medicine 7(1):119-122 (2001).

Coskun et al., "The first regio- and diastereoselective synthesis of homochiral perhydroimidazoisoxazoles via the 1,3-dipolar cycloaddition of imidazoline 3-oxides with (1S)-(−)-beta-pinen," Tetrahedron: Asymmetry 12:1463-1467 (2001).

(56) References Cited

OTHER PUBLICATIONS

Crall, Jr. et al., "The Extramural and Intramural Coronary Arteries in Juvenile Diabetes Mellitus," The American Journal of Medicine 64:221-230 (1978).
Database CAPLUS Abstract of Kuz'Menko et al., "Unusual decomposition of benzimidazolium phenacyl salts. Synthesis of 1,4-diarylimidazoles," Khimiya Geterotsiklicheskokh Soedinenii, No. 3, pp. 388-392 (1982).
Database CAPLUS on STN Abstract of Dobrev et al., "Addition of N,N-disubstituted amides to N-benzoyldiphenylketimine in the presence of lithium amide in liquid ammonia," God. Sofii. Univ., Khim. Fak. 70(1):201-207 (1978).
Database CAPLUS on STN Abstract of Frappier et al., "Peptide Alkaloids. X. Approach for the synthesis of peptidic alkaloids. 1. Reactivity of N-tolylsulfonylaziridines towards reactive nucleophiles," Tetrahedron 34(19):2911-2916 (1976).
Database CAPLUS on STN Abstract of Hamada et al., "Preparation of anilide derivatives for determination of enzymes," 1992.
Database CAPLUS on STN Abstract of Pirkle et al., "Separation of the enantiomers of N-protected alpha-amino acids as anilide and 3,5-dimethylanilide derivatives," Journal of Chromatography 479(2):419-423 (1989).
Database CAPLUS on STN Abstract of Sivanandaiah et al., "Synthesis of peptides mediated by KOBt," International Journal of Peptide and Protein Research 44(1):24-30 (1994).
Database CAPLUS on STN Abstract of Tsukida et al., "Aminocarboxylic acids, selectin inhibitors containing them, and their uses" (1999).
Database CAPLUS on STN Abstract of Vidugiriene et al., "Synthesis and study of derivatives of 3-(alkylamino)-2-(methylthio)carboxylic acids," Chemija 2:101-106 (1990).
Database HCAPLUS on STN Abstract of Katzenellenbogen et al., "Preparation of non-steroidal estrogen receptor subtype-selective ligands," Accession No. 2000:240935, Reg. No. 234093-17-5 (2000).
Deane et al., "RAGE mediated amyloid-beta peptide transport across the blood-brain barrier and accumulation in brain," Nature Medicine 9(7):907-913 (2003).
Degenhardt et al., "Chemical Modification of Proteins by Methylglyoxal," Cellular and Molecular Biology 44(7):1139-1145 (1998).
Denny et al., "Potential Antitumor Agents. 59. Structure-Activity Relationships for 2-Phenylbenzimidazole-4-carboxamides, a New Class of 'Minimal' DNA-Intercalating Agents Which May Not Act via Topoisomerase II," Journal of Medicinal Chemistry 33(2):814-819 (1990).
Digenis et al., "Peptidyl Carbamates Incorporating Amino Acid Isoteres as Novel Elastase Inhibitors," Journal of Medicinal Chemistry 29(8):1468-1476 (1986).
Dyer et al., "Accumulation of Maillard Reaction Products in Skin Collagen in Diabetes and Aging," J. Clin. Invest. 91:2463-2469 (1993).
Dyer et al., "Formation of Pentosidine during Nonenzymatic Browning of Proteins by Glucose," The Journal of Biological Chemistry 266(18):11654-11660 (1991).
Eriks et al., "Histamine H2-Receptor Agonists. Synthesis, in Vitro Pharmacology, and Qualitative Structure-Activity Relationships of Substituted 4- and 5-(2-Aminoethyl)thiazoles," J. Med. Chem. 35(17):3239-3246 (1992).
Evans et al., "Synthesis of a group of 1H-benzimidazoles and their screening for antiinflammatory activity," Eur. J. Med. Chem. 31:635-642 (1996).
Fang et al., "RAGE-dependent signaling in microglia contributes to neuroinflammation, A-beta accumulation, and impaired learning/memory in a mouse model of Alzheimer's disease," The FASEB Journal 24:1043-1055 (2010).
Fink et al., "Novel structural templates for estrogen-receptor ligands and prospects for combinatorial synthesis of estrogens," Chemistry & Biology 6(4):205-219 (1999).
Galasko et al., "Clinical-Neuropathological Correlations in Alzheimer's Disease and Related Dementias," Arch. Neurol. 51:888-895 (1994).
Games et al., "Alzheimer-type neuropathology in transgenic mice overexpressing V717F beta-amyloid precursor protein," Nature 373:523-527 (1995).
Girouard et al., "Neurovascular coupling in the normal brain and in hypertension, stroke, and Alzheimer disease," J. Appl. Physiol. 100:328-335 (2006).
Golub et al., "Molecular Classification of Cancer: Class Discovery and Class Prediction by Gene Expression Monitoring," Science 286:531-537 (1999).
Goova et al., "Blockade of Receptor for Advanced Glycation End-Products Restores Effective Wound Healing in Diabetic Mice," The American Journal of Pathology 159:513-525 (2001).
Greene et al., Protective Groups in Organic Synthesis, 2nd Ed., John Wiley & Sons, Inc., New York, Chapter 7, pp. 222-287 (1991).
Groutas et al., "Synthesis and Pharmacological Studies of N-[4[2-Hydroxy-3[[2-4-(1H-imidazol-1-yl)phenoxy]ethyl]amino]propoxy]phenyl]methanesulfonamide, a Novel Antiarrhythmic Agent with Class II and Class III Activities," J. Med. Chem. 33:1087-1090 (1990).
Gualtieri et al., "Antiviral Agents. 2. Analogs of 2-(alpha-Hydroxybenzyl)benzimidazole," Journal of Medicinal Chemistry 15(4):420-422 (1972).
Haass et al., "Cellular Processing of beta-Amyloid Precursor Protein and the Genesis of Amyloid beta-Peptide," Cell 75:1039-1042 (1993).
Hambly et al., "Reappraisal of the role of the diabetic state in coronary artery disease," Chest 70(2):251-257 (1976).
Hammes et al., "Diabetic retinopathy risk correlates with intracellular concentrations of the glycoxidation product N(epsilon)-(carboxymethyl) lysine independently of glycohaemoglobin concentrations," Diabetologia 42:603-607 (1999).
Heinze et al., "Synthesis of tetraaylimidazoles and pentaarylimidazoliu salts," Chemische Berichte 101(10):3504-3516 (1968).
Hofmann et al., "RAGE Mediates a Novel Proinflammatory Axis: A Central Cell Surface Receptor for S100/Calgranulin Polypeptides," Cell 97:889-901 (1999).
Hori et al., "The Receptor for Advanced Glycation End Products (RAGE) Is a Cellular Binding Site for Amphoterin," The Journal of Biological Chemistry 270(43):25752-25761 (1995).
Huttunen et al., "Receptor for Advanced Glycation End Products (RAGE)-mediated Neurite Outgrowth and Activation of NF-kB Require the Cytoplasmic Domain of the Receptor but Different Downstream Signaling Pathways," The Journal of Biological Chemistry 274(28):19919-19924 (1999).
International Preliminary Report on Patentability for related International Application No. PCT/2010/049934 mailed Apr. 12, 2012.
International Search Report and Written Opinion for related International Application No. PCT/US2010/049934 mailed Nov. 10, 2010.
Johnson et al., "MDL 29311: Antioxidant With Marked Lipid- and Glucose-Lowering Activity in Diabetic Rats and Mice," Diabetes 42:1179-1186 (1993).
Kamboh, "Molecular Genetics of Late-Onset Alzheimer's Disease," Annals of Human Genetics 98:381-404 (2004).
Kannel et al., "Diabetes and Cardiovascular Disease: The Framingham Study," JAMA 241(19):2035-2038 (1979).
Kannel et al., "Diabetics and Glucose Tolerance as Risk Factors for Cardiovascular Disease: The Framingham Study," Diabetics Care 2(2):120-126 (1979).
Kennedy et al., "Familial Alzheimer's disease," Brain 116:309-324 (1993).
Kislinger et al., "Receptor for Advanced Glycation End Products Mediates Inflammation and Enhanced Expression of Tissue Factor in Vasculature of Diabetic Apolipoprotein E-Null Mice," Arterioscler Thromb Vasc Biol. 21:905-910 (2001).
Kumar et al., "RAGE at the Blood-Brain Barrier Mediates Neurovascular Dysfunction Caused by Amyloid-beta1-40 Peptide," Neurosci. Program, p. 414-#275.19 (2000).

(56) References Cited

OTHER PUBLICATIONS

Lampe et al., "Cardiotonic Agents. 6. Histamine Analogues as Potential Cardiovascular Selective H2 Agonists," Journal of Medicinal Chemistry 33(6):1688-1697 (1990).
Lander et al., "Activation of the Receptor for Advanced Glycation End Products Triggers a p21(ras)-dependent Mitogen-activated Protein Kinase Pathway Regulated by Oxidant Stress," The Journal of Biological Chemistry 272(28):17810-17814 (1997).
Leder et al., "v-Ha-ras transgene abrogates the initiation step in mouse skin tumorigenesis: Effects of phorbol esters and retinoic acid," Proc. Natl. Acad. Sci. USA 87:9178-9182 (1990).
Levy-Lahad et al., "Candidate Gene for the Chromosome 1 Familial Alzheimer's Disease Locus," Science, New Series 269(5226):973-977 (1995).
Li et al., "Characterization and Functional Analysis of the Promoter of RAGE, the Receptor for Advanced Glycation End Products," The Journal of Biological Chemistry 272(26):16498-16506 (1997).
Li et al., "Sp1-binding Elements in the Promoter of RAGE Are Essential for Amphoterin-mediated Gene Expression in Cultured Neuroblastoma Cells," The Journal of Biological Chemistry 273:30870-30878 (1998).
Lugering et al., "The myleloic related protein MRP8/14 (27E10 antigen)—usefulness as a potential marker for disease activity in ulcerative colitis and putative biological function," European Journal of Clinical Investigation 25:659-664 (1995).
Mackic et al., "Human Blood-Brain Barrier Receptors for Alzheimer's Amyloid-beta 1-40: Asymmetrical Binding, Endocytosis, and Transcytosis at the Apical Side of Brain Microvascular Endothelial Cell Monolayer," J. Clin. Invest. 102(4):734-743 (1998).
McKhann et al., "Clinical diagnosis of Alzheimer's disease: Report of the NINCDS-ADRDA Work Group under the auspices of Department of Health and Human Services Task Force on Alzheimer's Disease," Neurology 34:939-944 (1984).
Miyata et al., "Beta2-Microglobulin Modified with Advanced Glycation End Products Is a Major Component of Hemodialysis-associated Amyloidosis," J. Clin. Invest. 92:1243-1252 (1993).
Miyata et al., "The Receptor for Advanced Glycation End Products (RAGE) Is a Central Mediator of the Interaction of AGE-beta2Microglobulin with Human Mononuclear Phagocytes Via an Oxidant-sensitive Pathway," J. Clin. Invest. 98(5):1088-1094 (1996).
Morcos et al., "Activation of Tubular Epithelial Cells in Diabetic Nephropathy," Diabetes 51:3532-3544 (2002).
Morris et al., "Place navigation impaired in rats with hippocampal lesions," Nature 297:681-683 (1982).
Needleman et al., "A General Method Applicable to the Search for Similarities in the Amino Acid Sequence of Two Proteins," J. Mol. Biol. 48:443-453 (1970).
Neeper et al., "Cloning and Expression of a Cell Surface Receptor for Advanced Glycosylation End Products of Proteins," The Journal of Biological Chemistry 267(21):14998-15004 (1992).
Ohkubo et al., "Studies on Cerebral Protective Agents. VII. Synthesis of Novel 4-Arylazole Derivatives with Anti-anoxic Activity," Chem. Pharm. Bull. 43(6):947-954 (1995).
Oldfield et al., "Advanced glycation end products cause epithelial-myofibroblast transdifferentiation via the receptor for advanced glycation end products (RAGE)," The Journal of Clinical Investigation 108(12):1853-1863 (2001).
Pappolla et al., "The Heat Shock/Oxidative Stress Connection: Relevance to Alzheimer Disease," Molecular and Chemical Neuropathology 28:21-34 (1996).
Park et al., "Suppression of accelerated diabetic atherosclerosis by the soluble receptor for advanced glycation endproducts," Nature Medicine 4(9):1025-1031 (1998).
Parkkinen et al., "Amphoterin, the 30-kDa Protein in a Family of HMG1-type Polypeptides, Enhanced Expression in Transformed Cells, Leading Edge Localization, and Interactions with Plasminogen Activation," The Journal of Biological Chemistry 268(26):19726-19738 (1993).
Pastor et al., "Molecular Genetics of Alzheimer's Disease," Current Psychiatry Reports 6:125-133 (2004).
Pearson et al., "Improved tools for biological sequence comparison," Proc. Natl. Acad. Sci. USA 85:2444-2448 (1988).
Penning et al., "Structure-Activity Relationship Studies on 1-[2-(4-Phenylphenoxy)ethyl]pyrrolidine (SC-22716), a Potent Inhibitor of Leukotriene A4 (LTA4) Hydrolase," J. Med. Chem. 43:721-735 (2000).
Pike et al., "Neurodegeneration Induced by beta-Amyloid Peptides in vitro: The Role of Peptide Assembly State," The Journal of Neuroscience 13(4):1676-1687 (1993).
Porretta et al., "Chemotherapeutic agents with an imidazole moiety. III. Synthesis and microbiological activity of new 1,4-diaryl-limidazole and 1,4-pyrrolimidazolephenylene derivatives," II Farmaco 46(7,8):913-924 (1991).
Pyorala et al., "Diabetes and Atherosclerosis: An Epidemiologic View," Diabetes/Metabolism Reviews 3(2):463-524 (1987).
Rammes et al., "Myeloid-related Protein (MRP) 8 and MRP14, Calcium-binding Proteins of the S100 Family, Are Secreted by Activated Monocytes via a Novel, Tubulin-dependent Pathway," The Journal of Biological Chemistry 272(14):9496-9502 (1997).
Ranginwala et al., "Clinical Criteria for the Diagnosis of Alzheimer Disease: Still Good After All These Years," Am. J. Geriatr. Psychiatry 16(5):384-388 (2008).
Rauvala et al., "Isolation and Some Characteristics of an Adhesive Factor of Brain That Enhances Neurite Outgrowth in Central Neurons," The Journal of Biological Chemistry 262(34):16625-16635 (1987).
Reddy et al., "N(epsilon)-(Carboxymethyl)lysine Is a Dominant Advanced Glycation End Product (AGE) Antigen in Tissue Proteins," Biochemistry 34:10872-10878 (1995).
Ritthaler et al., "Expression of Receptors for Advanced Glycation End Products in Peripheral Occlusive Vascular Disease," American Journal of Pathology 146(3):688-694 (1995).
Robertson et al., "Atherosclerosis in Persons with Hypertension and Diabetes Mellitus," Laboratory Investigation 18(5):538-551 (1968).
Rogaev et al., "Familial Alzheimer's disease in kindreds with missense mutations in a gene on chromosome 1 related to the Alzheimer's disease type 3 gene," Nature 376:775-778 (1995).
Sanfilippo et al., "Synthesis of (Aryloxy)alkylamines. 1. Novel Antisecretory Agents with H+K+-ATPase Inhibitory Activity," J. Med. Chem. 31:1778-1785 (1988).
Sanfilippo et al., "Synthesis of (Aryloxy)alkylamines. 2. Novel Imidazo-fused Heterocycles with Calcium Channel Blocking and Local Anesthetic Activity," J. Med. Chem. 31(11):2221-2227 (1988).
Schafer et al., "The S100 family of EF-hand calcium-binding proteins: functions and pathology," TIBS 21:134-140 (1996).
Schleicher et al., "Increased Accumulation of the Glycoxidation Product N(epsilon)-(carboxymethyl)lysine in Human Tissues in Diabetes and Aging," J. Clin. Invest. 99(3):457-468 (1997).
Schmidt et al., "Advanced Glycation Endproducts Interacting with Their Endothelial Receptor Induce Expression of Vascular Cell Adhesion Molecule-1(VCAM-1) in Cultured Human Endothelial Cells and in Mice," J. Clin. Invest. 96:1395-1403 (1995).
Schmidt et al., "Isolation and Characterization of Two Binding Proteins for Advanced Glycosylation End Products from Bovine Lung Which Are Present on the Endothelial Cell Surface," The Journal of Biological Chemistry 267(21):14987-14977 (1992).
Schmidt et al., "Receptor for advanced glycation end products (AGEs) has a central role in vessel wall interactions and gene activation in response to circulating AGE proteins," Proc. Natl. Acad. Sci. USA 91:8807-8811 (1994).
Schmidt et al., "The dark side of glucose," Nature Medicine 1(10):1002-1004 (1995).
Schmidt et al., "The role of RAGE in amyloid-beta peptide-mediated pathology in Alzheimer's disease," Current Opinion in Investigational Drugs 10(7):672-680 (2009).
Schmidt et al., "The V-Domain of Receptor for Advanced Glycation Endproducts (RAGE) Mediates Binding of AGEs: A Novel Target for Therapy of Diabetic Complications," Supplement to Circulation 96(8):Abstract No. 194 (1997).

(56) References Cited

OTHER PUBLICATIONS

Scozzafava et al., "Carbonic anhydrase activators—Part 21. Novel activators of isozymes I, II and IV incorporating carboxamido and ureido histamines moieties," Eur. J. Med. Chem. 35:31-39 (2000).
Selkoe, "Normal and Abnormal Biology of the beta-Amyloid Precursor Protein," Annual Review of Neuroscience 17:489-517 (1994).
Selkoe, "The Molecular Pathology of Alzheimer's Disease," Neuron 6:487-498 (1991).
Selkoe, "Translating cell biology into therapeutic advances in Alzheimer's disease," Nature 399:A23-31 (1999).
Semprini et al., "Evidence for differential S100 gene over-expression in psoriatic patients from genetically heterogeneous pedigrees," Hum. Genet. 111:310-313 (2002).
Sherrington et al., "Cloning of a gene bearing missense mutations in early-onset familial Alzheimer's disease," Nature 375:754-760 (1995).
Smith et al., "Comparison of Biosequences," Advances in Applied Mathematics 2:482-489 (1981).
Snowdon, "Healthy Aging and Dementia: Findings from the Nun Strudy," Annals of Internal Medicine 139(5):450-454 (2003).
Sousa et al., "Interaction of the Receptor for Advanced Glycation End Products (RAGE) with Transthyretin Triggers Nuclear Transcription Factor kB (NF-kB) Activation," Laboratory Investigation 80(7):1101-1110 (2000).
Strittmatter et al., "Apolipoprotein E: Highly-avidity binding to beta-amyloid and increased frequency of type 4 allele in late-onset familial Alzheimer disease," Proc. Natl. Acad. Sci. USA 90:1977-1981 (1993).
Taguchi et al., "Bloclade of RAGE-amphoterin signalling suppresses tumor growth and metastases," Nature 405:354-360 (2000).
Tanaka et al., "The Receptor for Advanced Glycation End Products Is Induced by the Glycation Products Themselves and Tumor Necrosis Factor-alpha through Nuclear Factor-kB, and by 17beta-Estradiol through Sp-1 in Human Vascular Endothelial Cells," The Journal of Biological Chemistry 275(33):25781-25790 (2000).
Teillet et al., "Food Restriction Prevents Advanced Glycation End Product Accumulation and Retards Kidney Aging in Lean Rats," J. Am. Soc. Nephrol. 11:1488-1497 (2000).
Varney et al., "Crystal-Structure-Based Design and Synthesis of Novel C-Terminal Inhibitors of HIV Protease," Journal of Medicinal Chemistry 37(15):2274-2284 (1994).
Vlassara, "Advanced Glycation End-products and Atherosclerosis," Annals of Medicine 28:419-426 (1996).
Waller et al., "Status of the Corornary Arteries at Necropsy in Diabetes Mellitus with Onset After Age 30 Years: Analysis of 229 Diabetic Patients With and Without Clinical Evidence of Coronary Heart Disease and Comparison to 183 Control Subjects," The American Journal of Medicine 69:498-506 (1980).
Wang et al., "The Polite of Soluble Amyloid beta Protein in Cultured Cell Media: Detection and Quantification of Amyloid beta Protein and Variants by Immunoprecipitation-Mass Spectrometry," The Journal of Biological Chemistry 271(50):31894-31902 (1996).
Wautier et al., "Advanced glycation end products (AGEs) on the surface of diabetic erhthrocytes bind to the vessel wall via a specific receptor inducing oxidant stress in the vasculature: A link between surface-associated AGEs and diabetic complications," Proc. Natl. Acad. Sci. USA 91:7742-7746 (1994).
Wautier et al., "Receptor-mediated Endothelial Cell Dysfunction in Diabetic Vasculopathy: Soluble Receptor for Advanced Glycation End Products Blocks Hyperpermeability in Diabetic Rats," J. Clin. Invest. 97(1):238-243 (1996).
Wiseniewski et al., "Apoplipoprotein E: a pathological chaperone protein in patients with cerebral and systemic amyloid," Neuroscience Letters 135:235-238 (1992).
Yan et al., "Amyloid-beta peptide-Receptor for Advanced Glycation Endproduct interaction elicits neuronal expression of macrophage-colony stimulating factor: A proinflammatory pathway in Alzheimer disease," Proc. Natl. Acad. Sci. USA 94:5296-5301 (1997)

Yan et al., "An intracellular protein that binds amyloid-beta peptide and mediates neurotoxicity in Alzheimer's disease," Nature 389:689-695 (1997).
Yan et al., "Enhanced Cellular Oxidant Stress by the Interaction of Advanced Glycation End Products with Their Receptors/Binding Proteins," The Journal of Biological Chemistry 269(13):9889-9897 (1994).
Yan et al., "RAGE and Alzheimer's Disease: A Progression Factor for Amyloid-beta-Induced Cellular Perturbation?" Journal of Alzheimer's Disease 16:833-843 (2009).
Yan et al., "RAGE and amyloid-beta peptide neurotoxicity in Alzheimer's disease," Nature 382:685-691 (1996).
Yan et al., "Receptor-dependent cell stress and amyloid accumulation in systemic amyloidosis," Nature 6(6):643-651 (2000).
Yankner et al., "Neurotrophic and Neurotoxic Effects of Amyloid beta Protein: Reversal by Tachykinin Neuropeptides," Science, New Series 250(4978):279-282 (1990).
Yeh et al., "Requirement for p38 and p44/p42 Mitogen-Activated Protein Kinases in RAGE-Mediated Nuclear Factor-kB Transcriptional Activation and Cytokine Secretion," Diabetes 50:1495-1504 (2001).
Zimmer et al., "The S100 Protein Family: History, Function, and Expression," Brain Research Bulletin 37(4):417-429 (1995).
Davis, et al., "RAGE Deletion Increases Anti-Oxidant and Anti-Inflammatory Biochemical Profiles in Human APP Transgenic Mice," Poster presented at Alzheimer's Association International Conference, Washington, DC, Jul. 20, 2015.
Sabbagh, M., "Evaluation of Phase 2b Safety of Azeliragon (TTP488)" presented at Clinical Trials on Alzheimer's Disease program, Barcelona, Spain, Nov. 6, 2015.
Amendment No. 6 to Form S-1 Registration Statement for vTv Therapeutics Inc., Jul. 24, 2015. pp. 1-2, 83, 86-94.
Investor Presentation—Jul. 2015. Slides 9-18.
Aricept® package insert, Feb. 2012.
Barile et al., "The RAGE Axis in Early Diabetic Retinopathy," Investigative Opththalmology & Visual Science 46(8):2916-2924 (2005).
Bishop et al., "Neural Mechanisms of ageing and cognitive decline," Nature 464:529-535 (2010).
Bonetta, "Door Slams on RAGE," Alzheimer Research Forum Print News, Nov. 9, 2011.
Burstein A, et al. "Azeliragon Phase 2b Survival Analysis Supports Beneficial Effects on Delaying Time to Cognitive Deterioration in Patients with Mild Alzheimer's Disease." Poster Presented at the Alzheimer's Association International Conference. Jul. 27, 2016. Toronto, Canada.
Burstein et al. "Evaluation of the relationship between TTP488 plasma concentration and changes in ADAS-cog relative to placebo." Poster session presented at: the Alzheimer's Association International Conference, Jul. 13-18, 2013, Boston, Massachusetts.
Burstein et al., "Effect of TTP488 in patients with mild to moderate Alzheimer's disease," BMC Neurology 14:12 (2014), 19 pages.
Donahue et al., "RAGE, LRP-1, and amyloid-beta protein in Alzheimer's disease," Acta Neuropathol. 112:405-415 (2006).
G. Basta et al., 63 Cardiovascular Research 582-592 (2004).
G.P. Sims et al., 28 Annual Review of Immunology, 367-368 (2010).
Galasko et al., "A clinical trial of an inhibitor of RAGE-A-beta interactions in Alzheimer's disease," RI clinical trialmanuscript, Aug. 8, 2012.
Galasko et al., "A Randomized Clinical Trial of an inhibitor of RAGE-A-beta interactions in patients with mild to moderate AD," DRAFT of presentation in Clinical Trials on Alzheimer's Disease program, San Diego, California, Nov. 3, 2011.
Galasko et al., "Clinical trial of an inhibitor of RAGE-A-beta interactions in Alzheimer disease," Neurology 82:1537-1542 (2014).
Galasko et al., Supplements 1-6 to "Clinical trial of an inhibitor of RAGE-A-beta interactions in Alzheimer disease," Neurology 82:1537-1542 (2014).
International Search Report and Written Opinion for related International Application No. PCT/US2013/062964, mailed Nov. 19, 2013.

(56) References Cited

OTHER PUBLICATIONS

Kostura et al. Efficacy of RAGE antagonist in murine model of Alzheimer's disease. Poster session presented at: the Alzheimer's Association International Congress; Jul. 13-18, 2014; Cophenhagen, Denmark.

Namenda® package insert, 2007, Jan. 2011.

Perrone et al., "The Complexity of Sporadic Alzheimer's Disease Pathogenesis: The Role of RAGE as Therapeutic Target to Promote Neuroprotection by Inhibiting Neurovascular Dysfunction," International Journal of Alzheimer's Disease, vol. 2012, 13 pages.

R. Ramasamy (Yan) et al., 15 Glycobiology 16R-18R (2005).

Sabbagh et al., "PF-04494700, an Oral Inhibitor of Receptor for Advanced Glycation End Products (RAGE), in Alzheimer Disease," Alzheimer Disease & Associated Disorders 25(3):206-212 (2011).

Spite et al., "Novel Lipid Mediators Promote Resolution of Acute Inflammation: Impact of Aspirin and Statins," Circulation Research, 107:1170-1184 (2010).

T. Wendt et al., 185 Atherosclerosis 70-77 (2006).

Takuma et al., "RAGE-mediated signaling contributes to intraneuronal transport of amyloid-beta and neuronal dysfunction," PNAS 106(47):20021-20026 (2009).

Thompson, A. J. et al., "Protein Conformational Misfolding and Amyloid Formation: Characteristics of a New Class of Disorders that Include Alzheimer's and Prion Diseases," Current Medicinal Chemistry, 9:1751-1762 (2002).

Vellas, et al., "Long-term changes in ADAS-cog: What is clinically relevant for disease modifying trails in Alzheimer?" (vol. 11, No. 4, 2007; Journal of Nutrition, Health & Aging).

SUBSTITUTED IMIDAZOLE DERIVATIVES AND METHODS OF USE THEREOF

FIELD OF THE INVENTION

This invention relates to compounds which are inhibitors of the interaction between the receptor for advanced glycation endproducts (RAGE) and its physiological ligands such as advanced glycated end products (AGEs), S100/calgranulin/EN-RAGE, β-amyloid, and amphoterin, for the treatment of RAGE mediated diseases.

BACKGROUND OF THE INVENTION

The Receptor for Advanced Glycated Endproducts (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., J. Biol. Chem. 267:14998-15004 (1992)). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al. (1995)). Increased levels of RAGE are also found in aging tissues (Schleicher et al., J. Clin. Invest. 99 (3): 457-468 (1997)), and the diabetic retina, vasculature and kidney (Schmidt et al., Nature Med. 1:1002-1004 (1995)). Activation of RAGE in different tissues and organs leads to a number of pathophysiological consequences. RAGE has been implicated in a variety of conditions including: acute and chronic inflammation (Hofmann et al., Cell 97:889-901 (1999)), the development of diabetic late complications such as increased vascular permeability (Wautier et al., J. Clin. Invest. 97:238-243 (1996)), nephropathy (Teillet et al., J. Am. Soc. Nephrol. 11:1488-1497 (2000)), atherosclerosis (Vlassara et. al., The Finnish Medical Society DUODECIM, Ann. Med. 28:419-426 (1996)), and retinopathy (Hammes et al., Diabetologia 42:603-607 (1999)). RAGE has also been implicated in Alzheimer's disease (Yan et al., Nature 382: 685-691 (1996)), erectile dysfunction, and in tumor invasion and metastasis (Taguchi et al., Nature 405: 354-357 (2000)).

Advanced glycation endproducts (AGEs) have been implicated in a variety of disorders including complications associated with diabetes and normal aging. Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as AGEs. Factors which promote formation of AGEs include delayed protein turnover (e.g. as in amyloidoses), accumulation of macromolecules having high lysine content, and high blood glucose levels (e.g. as in diabetes) (Hori et al., J. Biol. Chem. 270: 25752-761, (1995)).

AGEs display specific and saturable binding to cell surface receptors on endothelial cells of the microvasculature, monocytes and macrophages, smooth muscle cells, mesengial cells, and neurons.

In addition to AGEs, other compounds can bind to, and inhibit the interaction of physiological ligands with RAGE. In normal development, RAGE interacts with amphoterin, a polypeptide which mediates neurite outgrowth in cultured embryonic neurons (Hon et al., (1995)). RAGE has also been shown to interact with EN-RAGE, a protein having substantial similarity to calgranulin (Hofmann et al. (1999)). RAGE has also been shown to interact with β-amyloid (Yan et al., Nature 389:689-695 (1997); Yan et al., Nature 382: 685-691 (1996); Yan et al., Proc. Natl. Acad. Sci., 94:5296-5301 (1997)).

Binding of ligands such as AGEs, S100/calgranulin/EN-RAGE, β-amyloid, CML (Nε-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like.

In addition, several other regulatory pathways, such as those involving p21 ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Inhibiting binding of physiological ligands to RAGE provides for the down-regulation of the pathophysiological changes brought about by excessive concentrations of AGEs and other ligands for RAGE as described above.

Thus, there is a need for the development of compounds that inhibit the binding of physiological ligands to RAGE.

SUMMARY OF THE INVENTION

The present invention relates to compounds of Formula (I):

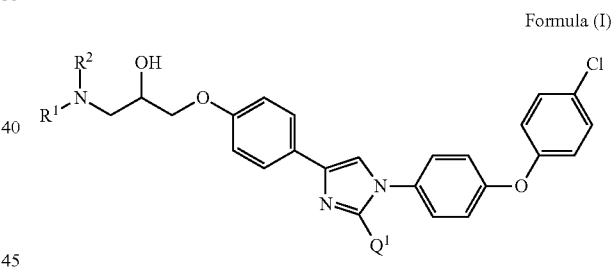

Formula (I)

or pharmaceutically acceptable salts thereof, wherein
$R^1$ and $R^2$ are independently selected from the group consisting of —CH$_3$, —CH$_2$CH$_3$, —CH(CH$_3$)$_2$, and —CH$_2$CH$_2$CH$_3$; and
$Q^1$ is selected from the group consisting of —CH$_2$OCH$_2$CH$_3$ and —CH$_2$CH$_2$CH$_2$CH$_3$.

This invention also provides for methods of preparation of compounds of Formula (I) or pharmaceutically acceptable salts thereof, pharmaceutical compositions comprising compounds of Formula (I) or pharmaceutically acceptable salts thereof; and methods for the use of compounds of Formula (I) or pharmaceutically acceptable salts thereof in treating diseases mediated by RAGE.

Compounds of Formula (I) or pharmaceutically acceptable salts thereof are useful as inhibitors of the interaction of the receptor for advanced glycation endproducts (RAGE) with ligands such as advanced glycated end products (AGEs), S100/calgranulin/EN-RAGE, β-amyloid, and amphoterin. The compounds are also useful in treating a variety of diseases or conditions in humans that may be responsive to the inhibition of RAGE. Such diseases or conditions include, but are not limited to, acute and chronic inflammation, the development of diabetic late complications such as increased vascular permeability, nephropathy, atherosclerosis, and retinopathy, the development of Alzheimer's disease and related disorders, erectile dysfunction, tumor invasion and metastasis, and osteoporosis.

The scope of the present invention includes combinations of the various aspects, embodiments, and preferences as herein described.

BRIEF DESCRIPTION OF DRAWINGS

Not applicable

DETAILED DESCRIPTION OF THE INVENTION

The following definitions are meant to clarify, but not limit, the terms defined. If a particular term used herein is not specifically defined, such term should not be considered indefinite. Rather, such terms are used within their plain and ordinary meanings.

As used herein, the various functional groups represented will be understood to have a point of attachment at the functional group having the hyphen. In other words, in the case of —CH$_2$CH$_2$CH$_3$, it will be understood that the point of attachment is the CH$_2$ group at the far left.

In a first embodiment, the present invention includes a compound of Formula (I):

Formula (I)

or a pharmaceutically acceptable salt thereof, wherein
$R^1$ and $R^2$ are independently selected from the group consisting of —CH$_3$, —CH$_2$CH$_3$, —CH(CH$_3$)$_2$, and —CH$_2$CH$_2$CH$_3$; and
$Q^1$ is selected from the group consisting of —CH$_2$OCH$_2$CH$_3$ and —CH$_2$CH$_2$CH$_3$.

In a second embodiment, the present invention provides a compound of Formula (I) or a pharmaceutically acceptable salt thereof wherein $R^1$ is —CH$_3$.

In a third embodiment, the present invention provides a compound of Formula (I) or a pharmaceutically acceptable salt thereof wherein $R^1$ is —CH$_2$CH$_3$.

In a fourth embodiment, the present invention provides a compound of Formula (I) or a pharmaceutically acceptable salt thereof according to any one of the previous embodiments wherein $R^2$ is —CH$_3$.

In a fifth embodiment, the present invention provides a compound of Formula (I) or a pharmaceutically acceptable salt thereof according to any one of the first to third embodiments wherein $R^2$ is —CH$_2$CH$_3$.

In a sixth embodiment, the present invention provides a compound of Formula (I) or a pharmaceutically acceptable salt thereof according to any one of the previous embodiments wherein $Q^1$ is —CH$_2$OCH$_2$CH$_3$.

In a seventh embodiment, the present invention provides a compound of Formula (I) or a pharmaceutically acceptable salt thereof according to any one of the first to fifth embodiments wherein $Q^1$ is —CH$_2$CH$_2$CH$_2$CH$_3$.

In an eighth embodiment, the present invention provides a compound of Formula (I) or a pharmaceutically acceptable salt thereof according to any one of the first to seventh embodiments wherein the compound is a free amine.

In a ninth embodiment, the present invention provides a compound of Formula (I) or a pharmaceutically acceptable salt thereof according to any one of the first to seventh embodiments wherein the compound is a pharmaceutically acceptable salt.

In a tenth embodiment, the present invention provides a compound of Formula (I) or a pharmaceutically acceptable salt thereof according to any one of the first to seventh embodiments wherein the compound is a hydrochloride salt.

In an eleventh embodiment, the present invention provides a compound of Formula (I) or a pharmaceutically acceptable salt thereof according to any one of the first to tenth embodiments wherein the group —CH$_2$CH(OH)CH$_2$NR$^1$R$^2$ is in the S configuration.

In a twelfth embodiment, the present invention provides a compound of Formula (I) or a pharmaceutically acceptable salt thereof according to any one of the first to tenth embodiments wherein the group —CH$_2$—CH(OH)—CH$_2$—NR$^1$R$^2$ is in the R configuration.

Specific embodiments of the compound of Formula (I) or a pharmaceutically acceptable salt thereof include:
(R)-1-(4-{2-butyl-1-[4-(4-chloro-phenoxy)-phenyl]-1H-imidazol-4-yl}-phenoxy)-3-dimethylamino-propan-2-ol;
(R)-1-(4-{2-butyl-1-[4-(4-chloro-phenoxy)-phenyl]-1H-imidazol-4-yl}-phenoxy)-3-diethylamino-propan-2-ol;
(S)-1-(4-{2-butyl-1-[4-(4-chloro-phenoxy)-phenyl]-1H-imidazol-4-yl}-phenoxy)-3-dimethylamino-propan-2-ol;
(S)-1-(4-{2-butyl-1-[4-(4-chloro-phenoxy)-phenyl]-1H-imidazol-4-yl}-phenoxy)-3-diethylamino-propan-2-ol;
(R)-1-(4-{1-[4-(4-chloro-phenoxy)-phenyl]-2-ethoxymethyl-1H-imidazol-4-yl}-phenoxy)-3-dimethylamino-propan-2-ol;
(S)-1-(4-{1-[4-(4-chloro-phenoxy)-phenyl]-2-ethoxymethyl-1H-imidazol-4-yl}-phenoxy)-3-dimethylamino-propan-2-ol;
(R)-1-(4-{1-[4-(4-chloro-phenoxy)-phenyl]-2-ethoxymethyl-1H-imidazol-4-yl}-phenoxy)-3-diethylamino-propan-2-ol; and
(S)-1-(4-{1-[4-(4-chloro-phenoxy)-phenyl]-2-ethoxymethyl-1H-imidazol-4-yl}-phenoxy)-3-diethylamino-propan-2-ol;
or a pharmaceutically acceptable salt thereof.

Another aspect of the present invention includes a pharmaceutical composition comprising a compound of Formula (I) or a pharmaceutically acceptable salt thereof and a pharmaceutically acceptable carrier.

One aspect of the present invention includes a method for treating a RAGE-mediated disease comprising administering to a subject a compound of Formula (I) or a pharmaceutically acceptable salt thereof. Another aspect includes use of a compound of Formula (I) or a pharmaceutically acceptable salt thereof for the manufacture of a medicament for treating a RAGE-mediated disease. A still further aspect includes a compound of Formula (I) or a pharmaceutically acceptable salt thereof for use in the treatment of a RAGE-mediated disease. In one embodiment, the disease is Alzheimer's Disease. In one embodiment, such treatment modifies the presentation of Alzheimer's Disease. In another embodiment, such treatment improves cognitive performance of a subject suffering from mild to moderate Alzheimer's Disease.

Pharmaceutically acceptable salts of the compounds of the present invention are also included within the scope of the invention. The term "pharmaceutically acceptable salt(s)" as used herein refers to non-toxic salts of a compound of Formula (I) which are generally prepared by reacting the free base (i.e. free amine) of the compound of Formula (I) with a suitable organic or inorganic acid such as, but not limited to, hydrochloride, hydrobromide, phosphate, sulfate, trifluoroacetate, trichloroacetate, acetate, oxalate, maleate, pyruvate, malonate, succinate, citrate, tartrate, fumarate, mandelate, benzoate, cinnamate, methiodide, methbromide, methchloride, methanesulfonate, ethanesulfonate, picrate and the like, and include acids related to the pharmaceutically-acceptable salts listed in the Journal of Pharmaceutical Science, 66, 2 (1977) p. 1-19. Other salts which are not pharmaceutically acceptable may be useful in the preparation of compounds of the invention and these form a further aspect of the invention.

Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}C$-or $^{14}C$-enriched carbon are within the scope of the invention.

The compound of Formula (I) contains one chiral center. The scope of the present invention includes mixtures of stereoisomers as well as purified enantiomers or enantiomerically/diastereomerically enriched mixtures. Also included within the scope of the invention are the individual isomers of the compounds represented by the formulae of the present invention, as well as any wholly or partially equilibrated mixtures thereof. The present invention also includes any tautomers of the compounds represented by the formulas above.

Examples of compounds of Formula (I) or a pharmaceutically acceptable salt thereof having potentially useful biological activity are herein described. The ability of compounds of Formula (I) or pharmaceutically acceptable salts thereof to inhibit the interaction of RAGE with its physiological ligands was established with representative compounds of Formula (I) or a pharmaceutically acceptable salt thereof using the assay(s) described in the Examples section below.

The invention further provides pharmaceutical compositions comprising a compound of Formula (I) or a pharmaceutically acceptable salt thereof. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions or suspensions, lotions, eye ointments and eye or ear drops, impregnated dressings and aerosols etc., containing the compounds of the invention are contemplated. These topical formulations may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 0.1% up to about 99% of the formulation. More usually they will form up to about 80% of the formulation. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids.

The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Compounds that antagonize the interaction of RAGE with its physiological ligands are potentially useful in treating diseases or conditions that may be responsive to the inhibiting of the RAGE receptor. The present invention provides a method of treatment comprising: administering to a subject a compound of Formula (I) or a pharmaceutically acceptable salt thereof. In an embodiment of this aspect, the present invention provides a method for the inhibition of the interaction of RAGE with its physiological ligands. In another embodiment of this aspect, the present invention provides a method for treating a disease state selected from the group consisting of acute and chronic inflammation including skin inflammation such as psoriasis, atopic dermatitis, inflammation associated with organ, tissue, or cell transplantation, and lung inflammation including, asthma and chronic obstructive pulmonary disease, sepsis, diabetes, diabetes related complications, renal failure, hyperlipidemic atherosclerosis associated with diabetes, neuronal cytotoxicity, restenosis, Down's syndrome, dementia associated with head trauma, amyotrophic lateral sclerosis, multiple sclerosis, amyloidosis, an autoimmune disease, wound healing, periodontal disease, neuropathy, neuronal degeneration, vascular permeability, nephropathy, atherosclerosis, retinopathy, Alzheimer's disease, erectile dysfunction, tumor invasion and/or metastasis, and osteoporosis which comprises administering to a subject a therapeutically effective amount of a compound of a compound of Formula (I) or a pharmaceutically acceptable salt thereof.

I. RAGE and the Complications of Diabetes

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., J. Clin. Invest., 91:2463-2469 (1993); Reddy, S., et al., Biochem., 34:10872-10878 (1995); Dyer, D., et al., J. Biol. Chem., 266:11654-11660 (1991); Degenhardt, T., et al., Cell Mol. Biol., 44:1139-1145 (1998)). Accumulation of AGEs in the vasculature can occur focally, as in the joint amyloid composed of AGE-β2-microglobulin found in patients with dialysis-related amyloidosis (Miyata, T., et al., J. Clin. Invest., 92:1243-1252 (1993); Miyata, T., et al., J. Clin. Invest., 98:1088-1094 (1996)), or generally, as exemplified by the vasculature and tissues of patients with diabetes (Schmidt, A-M., et al., Nature Med., 1:1002-1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., J. Biol. Chem., 272:16498-16506 (1997); Li, J., et al., J. Biol. Chem., 273:30870-30878 (1998); Tanaka, N., et al., J. Biol. Chem., 275:25781-25790 (2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in the Amyloidoses

Also as noted above, the compounds of the present invention are useful in treating amyloidoses and/or Alzheimer's Disease. RAGE appears to be a cell surface receptor which binds β-sheet fibrillar material regardless of the composition of the subunits (amyloid-β peptide, Aβ, amylin, serum amyloid A, prion-derived peptide) (Yan, S.-D., et al., Nature, 382:685-691 (1996); Yan, S-D., et al., Nat. Med., 6:643-651 (2000)). Deposition of amyloid has been shown to result in enhanced expression of RAGE. For example, in the brains of patients with Alzheimer's disease (AD), RAGE expression increases in neurons and glia (Yan, S.-D., et al., Nature 382:685-691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., Neurosci. Program, p141 (2000)). Inhibition of RAGE-amyloid interaction has been shown to decrease expression of cellular RAGE and cell stress markers (as well as NF-kB activation), and diminish amyloid deposition (Yan, S-D., et al., Nat. Med., 6:643-651 (2000)) suggesting a role for RAGE-amyloid interaction in both perturbation of cellular properties in an environment enriched for amyloid (even at early stages) as well as in amyloid accumulation.

In other studies using a mouse model of Alzheimer's Disease, it has been shown that RAGE antagonists can reverse the formation of plaques and the loss of cognition. In U.S. Patent Publication No. US 2005/0026811, small molecule RAGE antagonists were used to inhibit the progression of Aβ deposition and reduced the volume of pre-existing plaques in Alzheimer's Disease mice (US 2005/0026811 at ¶¶581-586). Furthermore, treatment with such small molecule RAGE antagonists improved cognition in these Alzheimer's Disease mouse models (US 2005/0026811 at ¶¶587-590). Thus, in a mouse model of Alzheimer's Disease, those mice who had developed Aβ plaques and cognitive loss and were treated with small molecule RAGE antagonists exhibited a reduction in plaque volume and an improvement in cognitive performance as compared to those Alzheimer's Disease mice who were not treated with the small molecule RAGE antagonists, showing that the RAGE antagonist compounds may delay or slow loss of cognitive performance, or may improve cognitive performance of a subject suffering from dementia of Alzheimer's type.

Also, it had been shown in both cellular assays and in animal studies that RAGE mediates the transcytosis of circulating Aβ across the blood-brain barrier (BBB). Such increased transcytosis of Aβ results in neuronal oxidant stress and sustained reductions in cerebral blood flow. The effects of RAGE can be inhibited by a RAGE modulator (e.g., anti-RAGE antibody or sRAGE) (see e.g., Mackic et al., J. Clin. Invest., 102:734-743 (1998); see also Kumar et al., Neurosci., Program, p 141 (2000)). These finding were confirmed by additional studies (see e.g., U.S. Pat. No. 6,825,164 at col. 17, line 48 to col. 18, line 43; Deane et al., Nature Medicine, 9:907-913 (2003)). Reduced cerebral perfusion can promote ischemic lesions which can act synergistically with Aβ to exacerbate dementia. Also, insufficient cerebral blood flow may alter Aβ trafficking across the blood brain barrier thereby reducing Aβ clearance and promoting accumulation of Aβ in brain (see Girouard and Iadecola, J. Appl. Physiol., 100, 328-335 (2006) at page 332). Thus, the increase in cerebral blood flow promoted by RAGE antagonists may reduce the symptoms or delay onset of development of Alzheimer's Disease, or both. For example, RAGE antagonists may delay or slow loss of cognitive performance, or may improve cognitive performance of a subject suffering from dementia of Alzheimer's type, or both.

III. RAGE and Propagation of the Immune/Inflammatory Response

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., TIBS, 21:134-140 (1996); Zimmer, D., et al., Brain Res. Bull., 37:417-429 (1995); Rammes, A., et al., J. Biol. Chem., 272:9496-9502 (1997); Lugering, N., et al., Eur. J. Clin. Invest., 25:659-664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade as implicated in the inflammatory diseases such as but not limited to rheumatoid arthritis and multiple sclerosis.

RAGE is also implicated in inflammatory diseases of the skin such as but not limited to atopic dermatitis, eczema, and psoriasis. Psoriasis in particular is characterized by inflamed itchy lesions. Psoriasis may be accompanied by arthropathic symptoms that are similar to those in seen in rheumatoid arthritis. There is considerable evidence that psoriasis is a polygenic autoimmune disorder. Psoriatic lesions are rich in cytokines, in particular IL-1 and IL-8, both potent proinflammatory mediators. IL-8 in particular is a chemotactic factor for neutrophils; neutrophils are also known to synthesize and secrete S100 proteins, one of the ligands for RAGE which is implicated in propagation of the immune and inflammatory response. Psoriasin, (S100A7) a new member of the S100 gene family, is a secreted protein isolated from psoriatic skin. Semprini et al. (Hum. Genet. 2002 October, 111(4-5), 310-3) have shown a linkage of psoriasis genetic susceptibility to distinct overexpression of S100 proteins in skin. Therefore, a modulator of RAGE would be expected to regulate the immune response in psoriasis.

IV. RAGE and Amphoterin

As noted above, the compounds of the present invention are useful in treating tumor and tumor metastasis. For example, amphoterin is a high mobility group I nonhistone chromosomal DNA binding protein (Rauvala, H., et al., J. Biol. Chem., 262:16625-16635 (1987); Parkikinen, J., et al., J. Biol. Chem. 268:19726-19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., Nature 405:354-360 (2000)), and spontaneously arising papillomas in mice expressing the v-Ha-ras transgene (Leder, A., et al., Proc. Natl. Acad. Sci., 87:9178-9182 (1990)).

V. RAGE and Respiratory Diseases

Airway inflammation is important in the pathogenesis of asthma. Such inflammation may give rise to significant exacerbations and increases in asthma severity, as well as to be a major factor in a decline in asthmatic status. In severe exacerbations of asthma there is an intense, mechanistically heterogeneous inflammatory response involving neutrophil and eosinophil accumulation and activation. Neutrophils are a significant source of S100 proteins, key ligands for RAGE implicated in the propagation of the immune response and inflammation. Therefore, modulators of RAGE would be expected to possess therapeutic value in the treatment of asthma. Further, the propagation step in the immune response in the lung driven by S100—RAGE interaction would be expected to lead to the activation and/or recruitment of inflammatory cells, such as neutrophils, which in chronic obstructive pulmonary diseases such as emphysema, are significant sources of damaging proteases. Therefore, a RAGE modulator would be expected possess potential in the treatment of chronic obstructive pulmonary diseases.

As used herein, the phrase "therapeutically effective amount" shall mean that amount of a drug or pharmaceutical agent that will elicit the therapeutic response of an subject that is being sought.

In these methods, factors which may influence what constitutes a therapeutically effective amount include, but are not limited to, the size and weight of the subject, the biodegradability of the therapeutic agent, the activity of the therapeutic agent, the size of the effected area, as well as its bioavailability. The phrase includes amounts which, as compared to a corresponding subject who has not received such amount, results in improved treatment, healing, or amelioration of a side effect, or a decrease in the rate of advancement of a disease or disorder.

In an embodiment, the present invention provides a method for treating restenosis comprising: administering to a subject a therapeutically effective amount of a compound of Formula (I) or a pharmaceutically acceptable salt thereof. In an embodiment, the subject is suffering from diabetes.

In an embodiment, the present invention provides a method for treating acute or chronic inflammation comprising: administering to a subject a therapeutically effective amount of a compound of Formula (I) or a pharmaceutically acceptable salt thereof.

In an embodiment, the present invention provides a method for treating dementia associated with head trauma comprising: administering to a subject a therapeutically effective amount of a compound of Formula (I) or a pharmaceutically acceptable salt thereof. In an embodiment, the cognitive performance of the subject is improved. In another embodiment, the cognitive performance of the subject is maintained. In another embodiment, the rate of loss of cognitive performance of the subject is slowed.

In an embodiment, the present invention provides a method for treating Alzheimer's Disease comprising: administering to a subject a therapeutically effective amount of a compound of Formula (I) or a pharmaceutically acceptable salt thereof. With respect to Alzheimer's Disease, the present invention is believed useful in alteration the course of the underlying dementing process. Alzheimer's Disease may be diagnosed by NINCDS and DSM criteria, Mini-Mental State Examination, and Clinical Dementia Rating within particular limits. One aspect of the present invention includes improving cognitive performance comprising administering a compound of Formula (I) or a pharmaceutically acceptable salt thereof. Cognitive performance may be assessed with the cognitive subscale of the Alzheimer's Disease Assessment Scale (ADAS-cog), as is known in the art, which scores cognitive function on a 0 to 70 scale, with higher scores indicating greater cognitive impairment. Thus, a reduction in score demonstrates cognitive improvement. One aspect of the present invention includes administering to a subject a compound of Formula (I) or a pharmaceutically acceptable salt thereof to reduce an ADAS-cog score of a subject in need of such reduction. Such a subject may be a human be suffering from dementia of Alzheimer's type, mild to moderate Alzheimer's Diseases, or severe Alzheimer's Disease.

In addition, the progression of Alzheimer's Disease may also be assessed in a human through examination of four areas of function: General, Cognitive, Behavioral, and Activities of Daily Living. Such an assessment may be performed using a Clinician's Interview Based Impression of Change (CIBIC or CIBIC plus). One aspect of the present invention includes improvement in subject's function comprising administering a compound of Formula (I) or a pharmaceutically acceptable salt thereof. In one embodiment, the subject's function is one or more of general, cognitive, behavioral, and activities of daily living.

In an embodiment, the present invention provides a method for improving wound healing in a diabetic subject comprising: administering to the subject a therapeutically effective amount of a compound of Formula (I) or a pharmaceutically acceptable salt thereof, so as to improve the rate of wound healing in the subject relative to an untreated wound.

In an embodiment, the present invention provides a method for treating in a subject inflammation associated with transplantation of an organ, a tissue or a plurality of cells from a first site to a second site comprising: administering to the subject a therapeutically effective amount of a compound of Formula (I) or a pharmaceutically acceptable salt thereof, so as to reduce inflammation in the subject. In an embodiment, the first and second sites are in different subjects. In another embodiment, the first and second sites are in the same subject. In another embodiment, the transplanted organ, cells or tissue comprise a cell or tissue of a pancreas, skin, liver, kidney, heart, bone marrow, blood, bone, muscle, artery, vein, cartilage, thyroid, nervous system, or stem cells.

In another embodiment, at least one compound of Formula (I) or a pharmaceutically acceptable salt thereof is utilized, either alone or in combination with one or more known therapeutic agents As used herein, the phrase "a subject" refers to mammalian subjects, preferably humans, who either suffer from one or more of the aforesaid diseases or disease states or are at risk for such.

In a further aspect of the present invention, the RAGE inhibitors of the invention may be used in adjuvant therapeutic or combination therapeutic treatments with other known therapeutic agents.

The following is a non-exhaustive listing of adjuvants and additional therapeutic agents which may be utilized in combination with the RAGE inhibitors of the present invention:

Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Anti-tumor antibodies Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic classifications of treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic classifications of treatment for Alzheimer's Disease
1. Cholinesterase Inhibitor: Tacrine, Donepezil
2. Antipsychotics: Haloperidol, Thioridazine
3. Antidepressants: Desipramine, Fluoxetine, Trazodone, Paroxetine
4. Anticonvulsants: Carbamazepine, Valproic acid In a further embodiment, the present invention provides a method of treating a RAGE mediated disease, the method comprising administering to a subject a therapeutically effective amount of a compound of Formula (I) or a pharmaceutically acceptable salt thereof in combination with a therapeutic agent selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

In a further embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Such other therapeutic agents may be administered by a like route or different route that the compound of Formula (I) or a pharmaceutically acceptable salt thereof. Where a compound of Formula (I) or a pharmaceutically acceptable salt thereof is used in combination with another therapeutic agent, the composition may contain the compound of Formula (I) or a pharmaceutically acceptable salt thereof in combination with the other therapeutic agent(s). Alternatively, where separate dosage formulations are used, the compound of Formula (I) or a pharmaceutically acceptable salt thereof and one or more additional therapeutic agents may be administered at essentially the same time (e.g., concurrently) or at separately staggered times (e.g., sequentially).

Generally speaking, a compound of Formula (I) or a pharmaceutically acceptable salt thereof may be administered at a dosage level of from about 0.003 to 500 mg/kg of the body weight of the subject being treated. In an embodiment, a compound of Formula (I) or a pharmaceutically acceptable salt thereof may be administered at a dosage range between about 0.003 and 200 mg/kg of body weight per day. In an embodiment, a compound of Formula (I) or a pharmaceutically acceptable salt thereof may be administered at a dosage range between about 0.1 to 100 mg/kg of body weight per day. The amount of active ingredient that may be combined with the carrier materials to produce a single dosage may vary depending upon the host treated and the particular mode of administration. For example, a formulation intended for oral administration to humans may contain 1 mg to 2 grams of a compound of Formula (I) or a pharmaceutically acceptable salt thereof with an appropriate and convenient amount of carrier material which may vary from about 5 to 95 percent of the total composition. A dosage form intended for topical administration to the skin may be prepared at 0.1% to 99% compound to topical excipient ratio. A dosage form intended for inhaled administration of 0.01 to 200 mg of compound in a suitable carrier to deliver an inhaled dosage of compound. Dosage unit forms of systemically delivered compound may generally contain between from about 5 mg to about 500 mg of active ingredient. This dosage may be individualized by the clinician based on the specific clinical condition of the subject being treated. Thus, it will be understood that the specific dosage level for any particular subject will depend upon a variety of factors including the activity of the specific compound employed, the age, body weight, general health, sex, diet, time of administration, route of administration, rate of excretion, drug combination, size of effected area and the severity of the particular disease undergoing therapy.

The compounds of this invention may be made by a variety of methods well known to those of ordinary skill in the art including the methods are set out below in the Examples.

In another aspect, the present invention also provides a method for the synthesis of compounds useful as intermediates in the preparation of compounds of the present invention along with methods for their preparation.

In an embodiment, the present invention provides a method for synthesizing a compound of Formula (I) or a pharmaceutically acceptable salt thereof

15

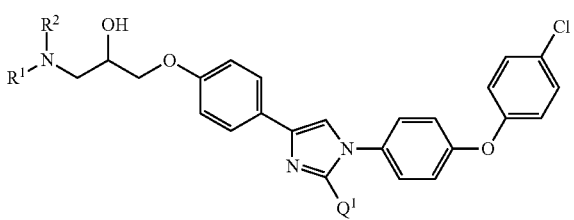

comprising: mixing a compound of Formula (X)

Formula (X)

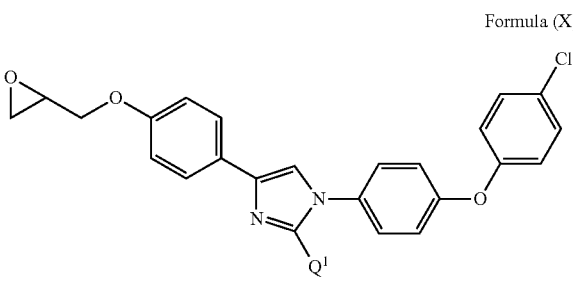

and an amine having the formula $R^1R^2NH$,
wherein
$R^1$ and $R^2$ are independently selected from the group consisting of $-CH_3$, $-CH_2CH_3$, $-CH(CH_3)_2$, and $-CH_2CH_2CH_3$; and
$Q^1$ is selected from the group consisting of $-CH_2OCH_2CH_3$ and $-CH_2CH_2CH_2CH_3$.

In an embodiment of the method of synthesis, $R^1$ and $R^2$ are the same.

In another embodiment of the method of synthesis, $R^1$ and $R^2$ are $-CH_3$.

In another embodiment of the method of synthesis, $R^1$ and $R^2$ are $-CH_2CH_3$.

In another embodiment of the method of synthesis, $Q^1$ is $-CH_2OCH_2CH_3$.

In another embodiment of the method of synthesis, $Q^1$ is $-CH_2CH_2CH_2CH_3$.

In another embodiment of the method of synthesis, the compound of Formula (X) is in the S configuration.

In another embodiment of the method of synthesis, the compound of Formula (X) is in the R configuration.

In another embodiment of the method of synthesis, mixture of the compound of Formula (X) and $R^1R^2NH$ is heated above room temperature. In a further embodiment, the mixture may be heated with microwave radiation.

In another embodiment of the method of synthesis, the compound of Formula (X) and $R^1R^2NH$ are mixed in a solvent. The solvent may be selected from an aprotic solvent. A suitable aprotic solvent includes THF.

EXAMPLES

LC-MS data were obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Sepax GP-C18 4.6×50 mm column. A three minute gradient may be run from 25% of solution B (97.5% acetonitrile, 2.5% water, 0.05% TFA) and 75% of solution A (97.5% water, 2.5% acetonitrile, 0.05% TFA) to 100% of solution B. The system is interfaced with a Waters Micromass ZQ mass spectrometer using electrospray ionization. All MS data was obtained in the positive mode unless otherwise noted.

$^1$H NMR data was obtained on a Varian 400 MHz spectrometer.

Abbreviations used in the Examples are as follows:

| | |
|---|---|
| d = | day |
| DCM = | dichloromethane |
| DMF = | N,N-dimethylformamide |
| DMSO = | dimethylsulfoxide |
| ELISA = | enzyme - linked immunosorbent assay |
| ether = | diethyl ether |
| EtOAc = | ethyl acetate |
| g = | gram |
| h = | hour |
| Hz = | hertz |
| L = | liter |
| LC = | liquid chromatography |
| M = | molar |
| m/z = | mass to charge ratio |
| MeOH = | methanol |
| mg = | milligram |
| min = | minute |
| mL = | milliliter |
| mM = | millimolar |
| mmol = | millimole |
| mol = | mole |
| MS = | mass spectrometry |
| N = | normal |
| NMR = | nuclear magnetic resonance spectroscopy |
| ppm = | parts per million |
| rt or RT = | room temperature |
| TFA = | trifluoroacetic acid |
| THF = | tetrahydrofuran |
| TLC = | thin layer chromatography |

Intermediate A1

4-{2-butyl-1-[4-(4-chloro-phenoxy)-phenyl]-1H-imidazol-4-yl}-phenol

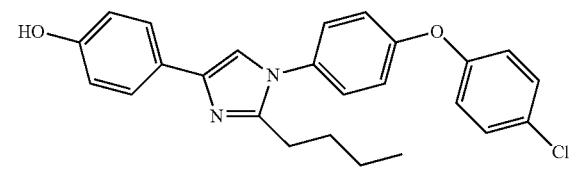 [SMILES: CCCCc1nc(-c2ccc(O)cc2)cn1-c1ccc(Oc2ccc(Cl)cc2)cc1]

Pyridinium bromide perbromide (33.6 g, 0.105 mole) was added to a solution of 4-acetylphenyl acetate (17.8 g, 0.1 mole) in dioxane (100 mL). The heterogeneous mixture was stirred for 5 hours. During the course of the reaction the intensity of the red color decreased and a white solid was formed. The reaction mixture was diluted with ether (200 mL) and washed with water (3×100 mL), brine (75 mL), dried (MgSO$_4$) and removed in vacuo to give the desired product as an oil, which solidified upon standing at room temperature (26.0 g). This product was used in the next transformation without further purification.

A solution of acetic acid 4-(2-bromo-acetyl)-phenyl ester (8.6 g, 33.6 mmol) in DCM (20 mL) was added to a mixture of 4-(4-chlorophenoxy)aniline (6.4 g, 29.2 mmol) and NaHCO$_3$ (4.2 g, 50 mmol) in methanol (100 mL). The formation of a yellow precipitate occurred after 1 h, but the reaction still did not go completion as indicated by both TLC and HPLC. The reaction mixture was further stirred overnight. The solvents were removed in vacuo and the residue was added to ice-water (200 g). The flask was then rinsed with more water (100 mL). After 1 hour, the yellow solid was collected by filtration and washed with water (200 mL). The filtrate (water) in the filtering flask was removed and vacuum kept going on for an hour to remove most of the water. To dry further, the solid was washed with isovaleryl ester, and the amide of the unreacted aniline.

A solution of acetic acid 4-{2-[4-(4-chloro-phenoxy)-phenylamino]-acetyl}-phenyl ester (79.17 g, 200 mmol, 1.0 eq.) in dichloromethane (800 mL) and triethylamine (56 mL, 400 mmol, 2.0 eq.) was cooled to –0° C. and treated with valeryl chloride (35.6 mL, 300 mmol, 1.5 eq.). The reaction mixture was stirred and warmed to room temperature over 24 h. This reaction mixture was then further treated with additional triethylamine (28 mL, 200 mmol, 1.0 eq.) and valeryl chloride (11.9 mL, 100 mmol, 0.5 eq.). Analysis of the reaction by TLC and LC/MS showed that some starting material remained, but the desired keto-amide was the major product. The reaction was evaporated in vacuo, recharged with ethyl acetate and filtered. The solvent was evaporated in vacuo, and the residue was then purified by flash column chromatography over silica gel (EtOAc/hexanes ~25%). The resultant oil was dissolved in ethyl acetate, washed with 1N HCl, dried and evaporated in vacuo. This material was then used as is in the next transformation.

A mixture of acetic acid 4-(2-{[4-(4-chloro-phenoxy)-phenyl]-pentanoyl-amino}-acetyl)-phenyl ester (from above, based on 200 mmol) with ammonium acetate (308 g, 4000 mmol, 20.0 eq) in acetic acid (300 mL) was stirred at 100-110° C. overnight. After completion of the reaction (indicated by HPLC), the mixture was cooled below 60° C. and poured over ice. After stirring, the solid was filtered, washed with diethyl ether (twice), ethyl acetate (twice), ether (once) and air dried, yielding ~55.0 g (65.6%) of 4-{2-butyl-1-[4-(4-chloro-phenoxy)-phenyl]-1H-imidazol-4-yl}-phenol as a finely divided off-white solid.

¹H-NMR (400 MHz; CDCl₃): δ 7.65 (d, 2H), 7.37 (d, 2H), 7.30 (d, 2H), 7.13 (s, 1H), 7.09 (d, 2H), 7.03 (d, 2H), 6.84 (d, 2H), 2.70-2.66 (m, 2H), 1.69-1.61 (m, 2H), 1.33-1.28 (m, 2H), 0.86 (t, 3H).

Intermediate A2

2-butyl-1-[4-(4-chloro-phenoxy)-phenyl]-4-[4-((R)-1-oxiranylmethoxy)-phenyl]-1H-imidazole

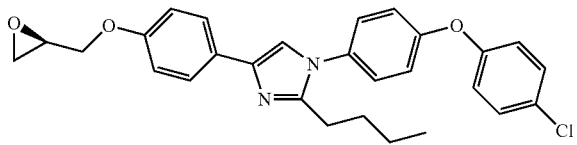 [SMILES: CCCCc1nc(-c2ccc(OC[C@H]3CO3)cc2)cn1-c1ccc(Oc2ccc(Cl)cc2)cc1]

A mixture of 4-{2-butyl-1-[4-(4-chloro-phenoxy)-phenyl]-1H-imidazol-4-yl}-phenol (0.42 g, 1.0 mmol, 1.0 eq.) and Cs₂CO₃ (1.0 g, 3.0 mmol, 3.0 eq.) in DMF (3 mL) was stirred and preheated to 80° C. The reaction mixture was then treated with a solution of (2R)-(−)-glycidyl tosylate (0.27 g, 1.2 mmol, 1.2 eq.) in 1 mL of DMF dropwise, and further stirred at 80° C. for ~30-60 min following completion of the addition. Analysis of the reaction by TLC and LC/MS showed that the starting phenol had been consumed and the desired alkylated-phenol was the major product. The reaction was then cooled and diluted with EtOAc and washed with brine. The organic phase was dried with Na₂SO₄ and evaporated in vacuo. The crude alkylated-phenol was then purified by flash column chromatography over silica gel (EtOAc/hexanes ~1:3).

¹H-NMR (400 MHz; CDCl₃): δ 7.72 (d, 2H), 7.36 (d, 2H), 7.30 (d, 2H), 7.15 (s, 1H), 7.09 (d, 2H), 7.03 (d, 2H), 6.94 (d, 2H), 4.26-4.22 (m, 1H), 4.02-3.98 (m, 1H), 3.40-3.36 (m, 1H), 2.92-2.90 (m, 1H), 2.79-2.77 (m, 1H), 2.69-2.65 (m, 2H), 1.71-1.63 (m, 2H), 1.37-1.27 (m, 2H), 0.86 (t, 3H).

Intermediate A3

2-butyl-1-[4-(4-chloro-phenoxy)-phenyl]-4-[4-((S)-1-oxiranylmethoxy)-phenyl]-1H-imidazole

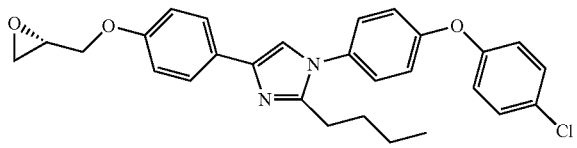 [SMILES: CCCCc1nc(-c2ccc(OC[C@@H]3CO3)cc2)cn1-c1ccc(Oc2ccc(Cl)cc2)cc1]

A mixture of 4-{2-butyl-1-[4-(4-chloro-phenoxy)-phenyl]-1H-imidazol-4-yl}-phenol (0.42 g, 1.0 mmol, 1.0 eq.) and Cs₂CO₃ (1.0 g, 3.0 mmol, 3.0 eq.) in DMF (3 mL) was stirred and preheated to 80° C. The reaction mixture was then treated with a solution of (2S)-(+)-glycidyl tosylate (0.27 g, 1.2 mmol, 1.2 eq.) in 1 mL of DMF dropwise, and further stirred at 80° C. for ~30-60 min following completion of the addition. Analysis of the reaction by TLC and LC/MS showed that the starting phenol had been consumed and the desired alkylated-phenol was the major product. The reaction was then cooled and diluted with EtOAc and washed with brine. The organic phase was dried with Na₂SO₄ and evaporated in vacuo. The crude alkylated-phenol was then purified by flash column chromatography over silica gel (EtOAc/hexanes ~1:3).

¹H-NMR (400 MHz; CDCl₃): δ 7.72 (d, 2H), 7.36 (d, 2H), 7.30 (d, 2H), 7.15 (s, 1H), 7.09 (d, 2H), 7.03 (d, 2H), 6.94 (d, 2H), 4.26-4.23 (m, 1H), 4.01-3.98 (m, 1H), 3.40-3.36 (m, 1H), 2.93-2.91 (m, 1H), 2.79-2.77 (m, 1H), 2.69-2.65 (m, 2H), 1.71-1.63 (m, 2H), 1.37-1.25 (m, 2H), 0.86 (t, 3H).

Intermediate B1

4-{1-[4-(4-chloro-phenoxy)-phenyl]-2-ethoxymethyl-1H-imidazol-4-yl}-phenol

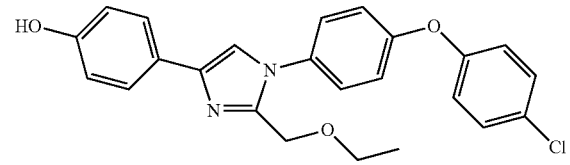 [SMILES: CCOCc1nc(-c2ccc(O)cc2)cn1-c1ccc(Oc2ccc(Cl)cc2)cc1]

Pyridinium bromide perbromide (33.6 g, 0.105 mole) was added to a solution of 4-acetylphenyl acetate (17.8 g, 0.1 mole) in dioxane (100 mL). The heterogeneous mixture was stirred for 5 hours. During the course of the reaction the intensity of the red color decreased and a white solid was formed. The reaction mixture was diluted with ether (200 mL) and washed with water (3×100 mL), brine (75 mL), dried (MgSO₄) and removed in vacuo to give the desired product as an oil, which solidified upon standing at room temperature (26.0 g). This product was used in the next transformation without further purification.

A solution of acetic acid 4-(2-bromo-acetyl)-phenyl ester (8.6 g, 33.6 mmol) in DCM (20 mL) was added to a mixture of 4-(4-chlorophenoxy)aniline (6.4 g, 29.2 mmol) and NaHCO$_3$ (4.2 g, 50 mmol) in methanol (100 mL). The formation of a yellow precipitate occurred after 1 h, but the reaction still did not go completion as indicated by both TLC and HPLC. The reaction mixture was further stirred overnight. The solvents were removed in vacuo and the residue was added to ice-water (200 g). The flask was then rinsed with more water (100 mL). After 1 hour, the yellow solid was collected by filtration and washed with water (200 mL). The filtrate (water) in the filtering flask was removed and vacuum kept going on for an hour to remove most of the water. To dry further, the solid was washed with isovaleryl ester, and the amide of the unreacted aniline.

A solution of acetic acid 4-{2-[4-(4-chloro-phenoxy)-phenylamino]-acetyl}-phenyl ester (0.33 mmol, 1.0 eq.) in THF (3 mL) was cooled to −78° C., treated with ethoxyacetyl chloride (0.33 mmol, 1.0 eq.) and stirred for ~5 min. This cold reaction mixture was then treated with pyridine (0.33 mmol, 1.0 eq.) dropwise and allowed to stir for ~1 h. Analysis of the reaction by TLC and LC/MS showed that the starting material has been consumed and the desired ketoamide was the major product. The reaction was then diluted with Et$_2$O and washed with H$_2$O, the organic phase was dried with Na$_2$SO$_4$ and evaporated in vacuo, and the crude keto-aniline was used in the subsequent step without further purification.

A mixture of N-(4-chlorophenoxyphenyl)-N-(4-acetoxybenzoylmethyl)-n-pentanamide (0.1011 mol, 1.0 eq) and ammonium acetate (175 g, 2.27 mol, 22.4 eq) in acetic acid (150 mL) was heated at 100-110° C. After completion of the reaction as indicated by HPLC or TLC, the mixture was cooled below 60° C. and is added to chilled water. The solid was filtered, washed with water and ethyl acetate and air dried to produce the desired 4-{1-[4-(4-chloro-phenoxy)-phenyl]-2-ethoxymethyl-1H-imidazol-4-yl}-phenol.

Intermediate B2

1-[4-(4-chloro-phenoxy)-phenyl]-2-ethoxymethyl-4-[4-((R)-1-oxiranylmethoxy)-phenyl]-1H-imidazole

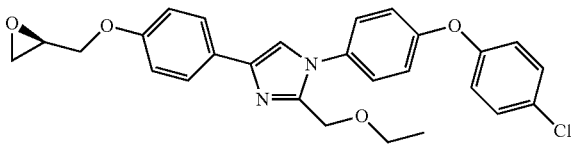 [SMILES: CCOCc1nc(-c2ccc(OC[C@H]3CO3)cc2)cn1-c1ccc(Oc2ccc(Cl)cc2)cc1]

A mixture of 4-{1-[4-(4-chloro-phenoxy)-phenyl]-2-ethoxymethyl-1H-imidazol-4-yl}-phenol (0.21 g, 0.5 mmol, 1.0 eq.) and Cs$_2$CO$_3$ (0.49 g, 1.5 mmol, 3.0 eq.) in DMF (2 mL) was stirred and preheated to 80° C. The reaction mixture was then treated with a solution of (2R)-(−)-glycidyl tosylate (0.17 g, 0.75 mmol, 1.5 eq.) in 1 mL of DMF dropwise, and further stirred at 80° C. for ~30 min following completion of the addition. Analysis of the reaction by TLC and LC/MS showed that the starting phenol had been consumed and the desired alkylated-phenol was the major product. The reaction was then cooled and diluted with EtOAc and washed with brine. The organic phase was dried with Na$_2$SO$_4$ and evaporated in vacuo. The crude alkylated-phenol was then purified by flash column chromatography over silica gel (EtOAc/hexanes ~1:3).

$^1$H-NMR (400 MHz; CDCl$_3$): δ 7.74 (d, 2H), 7.49 (d, 2H), 7.36 (d, 2H), 7.28 (s, 1H), 7.09 (d, 2H), 7.03 (d, 2H), 6.95 (d, 2H), 4.48 (s, 2H), 4.27-4.23 (m, 1H), 4.03-3.99 (m, 1H), 3.62-3.57 (m, 2H), 3.40-3.37 (m, 1H), 2.94-2.92 (m, 1H), 2.80-2.78 (m, 1H), 1.21 (t, 3H).

Intermediate B3

1-[4-(4-chloro-phenoxy)-phenyl]-2-ethoxymethyl-4-[4-((S)-1-oxiranylmethoxy)-phenyl]-1H-imidazole

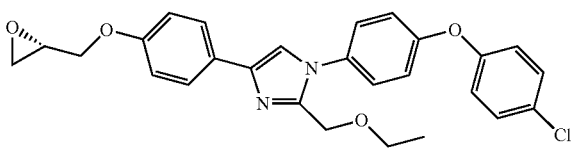 [SMILES: CCOCc1nc(-c2ccc(OC[C@@H]3CO3)cc2)cn1-c1ccc(Oc2ccc(Cl)cc2)cc1]

A mixture of 4-{1-[4-(4-chloro-phenoxy)-phenyl]-2-ethoxymethyl-1H-imidazol-4-yl}-phenol (0.21 g, 0.5 mmol, 1.0 eq.) and Cs$_2$CO$_3$ (0.49 g, 1.5 mmol, 3.0 eq.) in DMF (2 mL) was stirred and preheated to 80° C. The reaction mixture was then treated with a solution of (2S)-(+)-glycidyl tosylate (0.17 g, 0.75 mmol, 1.5 eq.) in 1 mL of DMF dropwise, and further stirred at 80° C. for ~30 min following completion of the addition. Analysis of the reaction by TLC and LC/MS showed that the starting phenol had been consumed and the desired alkylated-phenol was the major product. The reaction was then cooled and diluted with EtOAc and washed with brine. The organic phase was dried with Na$_2$SO$_4$ and evaporated in vacuo. The crude alkylated-phenol was then purified by flash column chromatography over silica gel (EtOAc/hexanes ~1:3).

$^1$H-NMR (400 MHz; CDCl$_3$): δ 7.74 (d, 2H), 7.49 (d, 2H), 7.36 (d, 2H), 7.28 (s, 1H), 7.09 (d, 2H), 7.03 (d, 2H), 6.95 (d, 2H), 4.48 (s, 2H), 4.27-4.24 (m, 1H), 4.03-3.99 (m, 1H), 3.62-3.57 (m, 2H), 3.40-3.37 (m, 1H), 2.94-2.92 (m, 1H), 2.80-2.78 (m, 1H), 1.20 (t, 3H).

Example 1

(R)-1-(4-{2-butyl-1-[4-(4-chloro-phenoxy)-phenyl]-1H-imidazol-4-yl}-phenoxy)-3-dimethylamino-propan-2-ol dihydrochloride

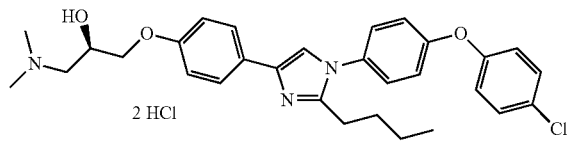 [SMILES: CCCCc1nc(-c2ccc(OC[C@H](O)CN(C)C)cc2)cn1-c1ccc(Oc2ccc(Cl)cc2)cc1]

A solution of 2-butyl-1-[4-(4-chloro-phenoxy)-phenyl]-4-[4-((R)-1-oxiranylmethoxy)-phenyl]-1H-imidazole (100 mg, 2.1 mmol, from intermediate A2) in 3 mL of dimethylamine in THF (2M) was stirred at 76° C. for 1 h in a microwave reactor. Upon completion (determined by LC/MS), the reaction was evaporated in vacuo and purified by silica gel flash column chromatography using a gradient of EtOAc to 96% EtOAc/(2M NH$_3$/MeOH) as an eluent to afford (R)-1-(4-{2-butyl-1-[4-(4-chloro-phenoxy)-phenyl]-1H-imidazol-4-yl}-phenoxy)-3-dimethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.62 (d, 2H), 7.44 (d, 2H), 7.23 (d, 2H), 7.16-7.10 (m, 4H), 4.39 (m, 1H), 4.09 (d, 2H), 3.37 (d, 2H), 2.98-2.96 (m, 8H), 1.69-1.66 (m, 2H), 1.37-1.31 (m, 2H), 0.88 (t, 3H).

Example 2

(R)-1-(4-{2-butyl-1-[4-(4-chloro-phenoxy)-phenyl]-1H-imidazol-4-yl}-phenoxy)-3-diethylamino-propan-2-ol dihydrochloride

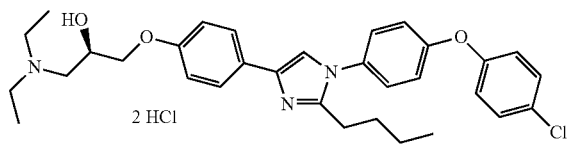 [SMILES: CCCCc1nc(-c2ccc(OC[C@H](O)CN(CC)CC)cc2)cn1-c1ccc(Oc2ccc(Cl)cc2)cc1]

A solution of 2-butyl-1-[4-(4-chloro-phenoxy)-phenyl]-4-[4-((R)-1-oxiranylmethoxy)-phenyl]-1H-imidazole (100 mg, 2.1 mmol, from intermediate A2) in 1 mL of diethylamine and 2 mL of THF was stirred at 76° C. for 1 h in a microwave reactor. Upon completion (determined by LC/MS), the reaction was evaporated in vacuo and purified by silica gel flash column chromatography using a gradient of EtOAc to 96% EtOAc/(2M NH$_3$/MeOH) as an eluent to afford (R)-1-(4-{2-butyl-1-[4-(4-chloro-phenoxy)-phenyl]-1H-imidazol-4-yl}-phenoxy)-3-diethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.74 (d, 2H), 7.62 (d, 2H), 7.45 (d, 2H), 7.24 (d, 2H), 7.17-7.10 (m, 4H), 4.42-4.38 (m, 1H), 4.11 (d, 2H), 3.45-3.27 (m, 6H), 2.97 (t, 2H), 1.72-1.64 (m, 2H), 1.39-1.30 (m, 8H), 0.89 (t, 3H).

Example 3

(S)-1-(4-{2-butyl-1-[4-(4-chloro-phenoxy)-phenyl]-1H-imidazol-4-yl}-phenoxy)-3-dimethylamino-propan-2-ol dihydrochloride

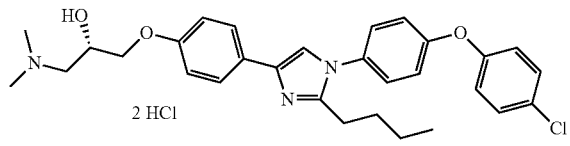 [SMILES: CCCCc1nc(-c2ccc(OC[C@@H](O)CN(C)C)cc2)cn1-c1ccc(Oc2ccc(Cl)cc2)cc1]

A solution of 2-butyl-1-[4-(4-chloro-phenoxy)-phenyl]-4-[4-((S)-1-oxiranylmethoxy)-phenyl]-1H-imidazole (from intermediate A3) in 3 mL of dimethylamine in THF (2M) was stirred at 76° C. for 1 h in a microwave reactor. Upon completion (determined by LC/MS), the reaction was evaporated in vacuo and purified by silica gel flash column chromatography using a gradient of EtOAc to 96% EtOAc/(2M NH$_3$/MeOH) as an eluent to afford (S)-1-(4-{2-butyl-1-[4-(4-chloro-phenoxy)-phenyl]-1H-imidazol-4-yl}-phenoxy)-3-dimethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.44 (d, 2H), 7.23 (d, 2H), 7.16-7.10 (m, 4H), 4.38 (m, 1H), 4.09 (d, 2H), 3.37 (d, 2H), 2.98-2.96 (m, 8H), 1.71-1.63 (m, 2H), 1.37-1.30 (m, 2H), 0.88 (t, 3H).

Example 4

(S)-1-(4-{2-butyl-1-[4-(4-chloro-phenoxy)-phenyl]-1H-imidazol-4-yl}-phenoxy)-3-diethylamino-propan-2-ol dihydrochloride

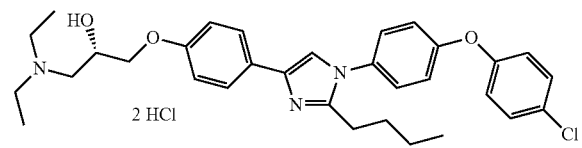 [SMILES: CCCCc1nc(-c2ccc(OC[C@@H](O)CN(CC)CC)cc2)cn1-c1ccc(Oc2ccc(Cl)cc2)cc1]

A solution of 2-butyl-1-[4-(4-chloro-phenoxy)-phenyl]-4-[4-((S)-1-oxiranylmethoxy)-phenyl]-1H-imidazole (from intermediate A3) in 1 mL of diethylamine and 2 mL of THF was stirred at 76° C. for 1 h in a microwave reactor. Upon completion (determined by LC/MS), the reaction was evaporated in vacuo and purified by silica gel flash column chromatography using a gradient of EtOAc to 96% EtOAc/(2M NH$_3$/MeOH) as an eluent to afford (S)-1-(4-{2-butyl-1-[4-(4-chloro-phenoxy)-phenyl]-1H-imidazol-4-yl}-phenoxy)-3-diethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.45 (d, 2H), 7.24 (d, 2H), 7.16-7.10 (m, 4H), 4.42-4.37 (m, 1H), 4.10 (d, 2H), 3.42-3.26 (m, 6H), 2.96 (t, 2H), 1.71-1.63 (m, 2H), 1.38-1.31 (m, 8H), 0.88 (t, 3H).

Example 5

(R)-1-(4-{1-[4-(4-chloro-phenoxy)-phenyl]-2-ethoxymethyl-1H-imidazol-4-yl}-phenoxy)-3-dimethylamino-propan-2-ol dihydrochloride

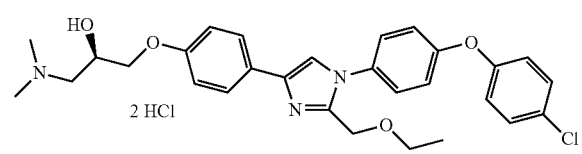 [SMILES: CCOCc1nc(-c2ccc(OC[C@H](O)CN(C)C)cc2)cn1-c1ccc(Oc2ccc(Cl)cc2)cc1]

A solution of 1-[4-(4-chloro-phenoxy)-phenyl]-2-ethoxymethyl-4-[4-((R)-1-oxiranylmethoxy)-phenyl]-1H-imidazole (~100 mg, ~0.20 mmol, from intermediate B2) in 3 mL of dimethylamine in THF (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{1-[4-(4-chloro-phenoxy)-phenyl]-2-ethoxymethyl-1H-imidazol-4-yl}-phenoxy)-3-dimethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^{1}$H-NMR (400 MHz; CD$_3$OD): δ 8.05 (s, 1H), 7.75 (d, 2H), 7.65 (d, 2H), 7.44 (d, 2H), 7.23 (d, 2H), 7.16-7.10 (m, 4H), 4.69 (s, 2H), 4.42-4.36 (m, 1H), 4.11 (d, 2H), 3.60 (q, 2H), 3.37 (d, 2H), 2.99 (s, 3H), 2.96 (s, 3H) 1.20 (t, 3H).

Example 6

(S)-1-(4-{1-[4-(4-chloro-phenoxy)-phenyl]-2-ethoxymethyl-1H-imidazol-4-yl}-phenoxy)-3-dimethylamino-propan-2-ol dihydrochloride

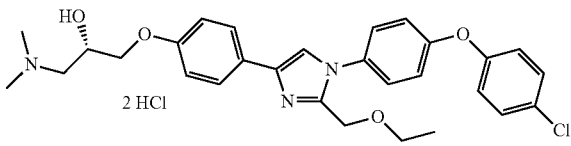

A solution of 1-[4-(4-chloro-phenoxy)-phenyl]-2-ethoxymethyl-4-[4-((S)-1-oxiranylmethoxy)-phenyl]-1H-imidazole (~100 mg, ~0.20 mmol, from intermediate B3) in 3 mL of dimethylamine in THF (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{1-[4-(4-chloro-phenoxy)-phenyl]-2-ethoxymethyl-1H-imidazol-4-yl}-phenoxy)-3-dimethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^{1}$H-NMR (400 MHz; CD$_3$OD): δ 8.05 (s, 1H), 7.76 (d, 2H), 7.65 (d, 2H), 7.44 (d, 2H), 7.23 (d, 2H), 7.16-7.10 (m, 4H), 4.69 (s, 2H), 4.42-4.36 (m, 1H), 4.10 (d, 2H), 3.60 (q, 2H), 3.37 (d, 2H), 2.99 (s, 3H), 2.96 (s, 3H) 1.20 (t, 3H).

Example 7

(R)-1-(4-{1-[4-(4-chloro-phenoxy)-phenyl]-2-ethoxymethyl-1H-imidazol-4-yl}-phenoxy)-3-diethylamino-propan-2-ol dihydrochloride

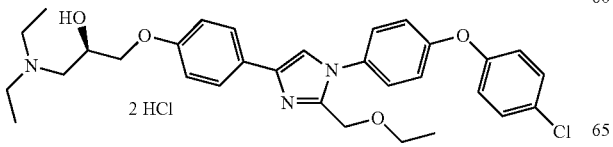

A solution of 1-[4-(4-chloro-phenoxy)-phenyl]-2-ethoxymethyl-4-[4-((R)-1-oxiranylmethoxy)-phenyl]-1H-imidazole (~100 mg, ~0.20 mmol, from intermediate B2) in 1 mL of diethylamine and 2 mL of THF was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{1-[4-(4-chloro-phenoxy)-phenyl]-2-ethoxymethyl-1H-imidazol-4-yl}-phenoxy)-3-diethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^{1}$H-NMR (400 MHz; CD$_3$OD): δ 8.06 (s, 1H), 7.76 (d, 2H), 7.66 (d, 2H), 7.43 (d, 2H), 7.22 (d, 2H), 7.16 (d, 2H), 7.10 (d, 2H), 4.69 (s, 2H), 4.42-4.36 (m, 1H), 4.11 (d, 2H), 3.62-3.56 (q, 2H), 3.41-3.24 (m 6H), 1.36 (t, 6H), 1.19 (t, 3H).

Example 8

(S)-1-(4-{1-[4-(4-chloro-phenoxy)-phenyl]-2-ethoxymethyl-1H-imidazol-4-yl}-phenoxy)-3-diethylamino-propan-2-ol dihydrochloride

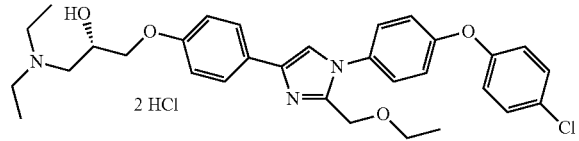 [SMILES: CCOCc1nc(-c2ccc(OC[C@@H](O)CN(CC)CC)cc2)cn1-c1ccc(Oc2ccc(Cl)cc2)cc1]

A solution of 1-[4-(4-chloro-phenoxy)-phenyl]-2-ethoxymethyl-4-[4-((S)-1-oxiranylmethoxy)-phenyl]-1H-imidazole (~100 mg, ~0.20 mmol, from intermediate B3) in 1 mL of diethylamine and 2 mL of THF was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{1-[4-(4-chloro-phenoxy)-phenyl]-2-ethoxymethyl-1H-imidazol-4-yl}-phenoxy)-3-diethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^{1}$H-NMR (400 MHz; CD$_3$OD): δ 8.06 (s, 1H), 7.75 (d, 2H), 7.65 (d, 2H), 7.43 (d, 2H), 7.22 (d, 2H), 7.16 (d, 2H), 7.10 (d, 2H), 4.69 (s, 2H), 4.42-4.36 (m, 1H), 4.11 (d, 2H), 3.62-3.56 (q, 2H), 3.41-3.24 (m, 6H), 1.36 (t, 6H), 1.19 (t, 3H).

Example 9

(R)-1-(4-{2-butyl-1-[4-(4-chloro-phenoxy)-phenyl]-1H-imidazol-4-yl}-phenoxy)-3-methylamino-propan-2-ol dihydrochloride

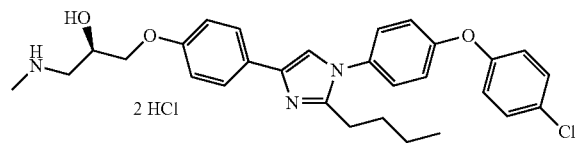 [SMILES: CCCCc1nc(-c2ccc(OC[C@H](O)CNC)cc2)cn1-c1ccc(Oc2ccc(Cl)cc2)cc1]

A solution of 2-butyl-1-[4-(4-chloro-phenoxy)-phenyl]-4-[4-((R)-1-oxiranylmethoxy)-phenyl]-1H-imidazole (50 mg, 0.11 mmol, from intermediate A2) in 4 mL of methylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{2-butyl-1-[4-(4-chloro-phenoxy)-phenyl]-1H-imidazol-4-yl}-phenoxy)-3-methylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.43 (d, 2H), 7.23 (d, 2H), 7.15-7.10 (m, 4H), 4.34-4.24 (m, 1H), 4.14-4.06 (m, 2H), 3.30-3.16 (m, 2H), 2.96 (t, 2H), 2.76 (s, 3H), 1.70-1.63 (m, 2H), 1.40-1.28 (m, 2H), 0.87 (t, 3H).

Example 10

(S)-1-(4-{2-butyl-1-[4-(4-chloro-phenoxy)-phenyl]-1H-imidazol-4-yl}-phenoxy)-3-methylamino-propan-2-ol dihydrochloride

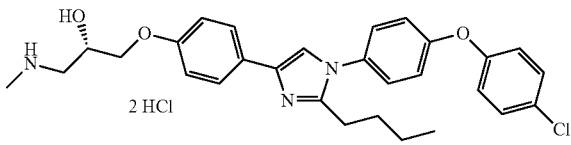 [SMILES: CCCCc1nc(-c2ccc(OC[C@@H](O)CNC)cc2)cn1-c1ccc(Oc2ccc(Cl)cc2)cc1]

A solution of 2-butyl-1-[4-(4-chloro-phenoxy)-phenyl]-4-[4-((S)-1-oxiranylmethoxy)-phenyl]-1H-imidazole (50 mg, 0.11 mmol, from intermediate A3) in 4 mL of methylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{2-butyl-1-[4-(4-chloro-phenoxy)-phenyl]-1H-imidazol-4-yl}-phenoxy)-3-methylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.43 (d, 2H), 7.23 (d, 2H), 7.15-7.10 (m, 4H), 4.34-4.24 (m, 1H), 4.12-4.06 (m, 2H), 3.30-3.16 (m, 2H), 2.96 (t, 2H), 2.76 (s, 3H), 1.70-1.63 (m, 2H), 1.40-1.28 (m, 2H), 0.87 (t, 3H).

Example 11

(R)-1-(4-{2-butyl-1-[4-(4-chloro-phenoxy)-phenyl]-1H-imidazol-4-yl}-phenoxy)-3-ethylamino-propan-2-ol dihydrochloride

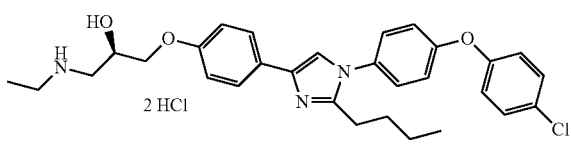 [SMILES: CCCCc1nc(-c2ccc(OC[C@H](O)CNCC)cc2)cn1-c1ccc(Oc2ccc(Cl)cc2)cc1]

A solution of 2-butyl-1-[4-(4-chloro-phenoxy)-phenyl]-4-[4-((R)-1-oxiranylmethoxy)-phenyl]-1H-imidazole (50 mg, 0.11 mmol, from intermediate A2) in 4 mL of ethylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{2-butyl-1-[4-(4-chloro-phenoxy)-phenyl]-1H-imidazol-4-yl}-phenoxy)-3-ethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.44 (d, 2H), 7.23 (d, 2H), 7.15-7.10 (m, 4H), 4.34-4.24 (m, 1H), 4.14-4.06 (m, 2H), 3.34-3.28 (m, 1H), 3.19-3.11 (m, 3H), 2.96 (t, 2H), 1.71-1.63 (m, 2H), 1.38-1.30 (m, 5H), 0.88 (t, 3H).

Example 12

(S)-1-(4-{2-butyl-1-[4-(4-chloro-phenoxy)-phenyl]-1H-imidazol-4-yl}-phenoxy)-3-ethylamino-propan-2-ol dihydrochloride

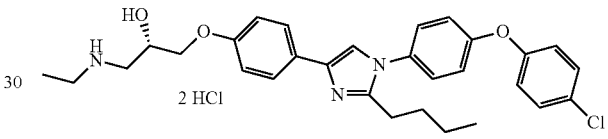

A solution of 2-butyl-1-[4-(4-chloro-phenoxy)-phenyl]-4-[4-((S)-1-oxiranylmethoxy)-phenyl]-1H-imidazole (50 mg, 0.11 mmol, from intermediate A3) in 4 mL of ethylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{2-butyl-1-[4-(4-chloro-phenoxy)-phenyl]-1H-imidazol-4-yl}-phenoxy)-3-ethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 7.90 (s, 1H), 7.73 (d, 2H), 7.61 (d, 2H), 7.44 (d, 2H), 7.23 (d, 2H), 7.16-7.10 (m, 4H), 4.34-4.24 (m, 1H), 4.14-4.06 (m, 2H), 3.34-3.28 (m, 1H), 3.18-3.11 (m, 3H), 2.96 (t, 2H), 1.71-1.63 (m, 2H), 1.38-1.29 (m, 5H), 0.88 (t, 3H).

Example 13

(R)-1-(4-{1-[4-(4-chloro-phenoxy)-phenyl]-2-ethoxymethyl-1H-imidazol-4-yl}-phenoxy)-3-methylamino-propan-2-ol dihydrochloride

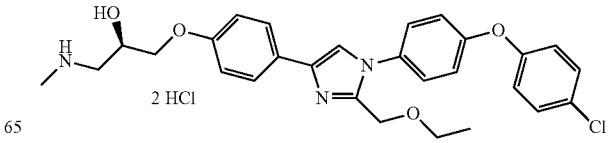

A solution of 1-[4-(4-chloro-phenoxy)-phenyl]-2-ethoxymethyl-4-[4-((R)-1-oxiranylmethoxy)-phenyl]-1H-imidazole (50 mg, 0.11 mmol, from intermediate B2) in 4 mL of methylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{1-[4-(4-chloro-phenoxy)-phenyl]-2-ethoxymethyl-1H-imidazol-4-yl}-phenoxy)-3-methylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 8.06 (s, 1H), 7.75 (d, 2H), 7.65 (d, 2H), 7.43 (d, 2H), 7.23 (d, 2H), 7.16-7.10 (m, 4H), 4.69 (s, 2H), 4.31-4.26 (m, 1H), 4.13-4.07 (m, 2H), 3.60 (q, 2H), 3.32-3.28 (m, 1H), 3.21-3.15 (m, 1H), 2.76 (s, 3H), 1.19 (t, 3H).

Example 14

(S)-1-(4-{1-[4-(4-chloro-phenoxy)-phenyl]-2-ethoxymethyl-1H-imidazol-4-yl}-phenoxy)-3-methylamino-propan-2-ol dihydrochloride

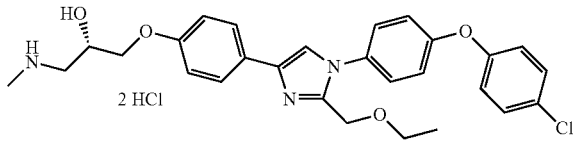 [SMILES: CCOCc1nc(-c2ccc(OC[C@@H](O)CNC)cc2)cn1-c1ccc(Oc2ccc(Cl)cc2)cc1]

A solution of 1-[4-(4-chloro-phenoxy)-phenyl]-2-ethoxymethyl-4-[4-((S)-1-oxiranylmethoxy)-phenyl]-1H-imidazole (50 mg, 0.11 mmol, from intermediate B3) in 4 mL of methylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{1-[4-(4-Chloro-phenoxy)-phenyl]-2-ethoxymethyl-1H-imidazol-4-yl}-phenoxy)-3-methylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 8.06 (s, 1H), 7.75 (d, 2H), 7.65 (d, 2H), 7.44 (d, 2H), 7.23 (d, 2H), 7.16-7.10 (m, 4H), 4.69 (s, 2H), 4.31-4.26 (m, 1H), 4.13-4.07 (m, 2H), 3.60 (q, 2H), 3.32-3.28 (m, 1H), 3.21-3.15 (m, 1H), 2.76 (s, 3H), 1.20 (t, 3H).

Example 15

(R)-1-(4-{1-[4-(4-chloro-phenoxy)-phenyl]-2-ethoxymethyl-1H-imidazol-4-yl}-phenoxy)-3-ethylamino-propan-2-ol dihydrochloride

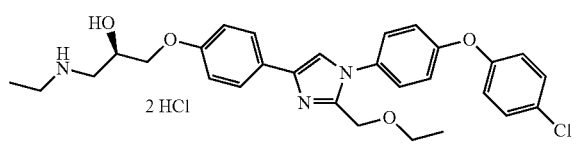 [SMILES: CCNC[C@@H](O)COc1ccc(-c2cn(-c3ccc(Oc4ccc(Cl)cc4)cc3)c(COCC)n2)cc1]

A solution of 1-[4-(4-chloro-phenoxy)-phenyl]-2-ethoxymethyl-4-[4-((R)-1-oxiranylmethoxy)-phenyl]-1H-imidazole (50 mg, 0.11 mmol, from intermediate B2) in 4 mL of ethylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (R)-1-(4-{1-[4-(4-Chloro-phenoxy)-phenyl]-2-ethoxymethyl-1H-imidazol-4-yl}-phenoxy)-3-ethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 8.02 (s, 1H), 7.75 (d, 2H), 7.64 (d, 2H), 7.44 (d, 2H), 7.23 (d, 2H), 7.16-7.10 (m, 4H), 4.67 (s, 2H), 4.29-4.25 (m, 1H), 4.13-4.06 (m, 2H), 3.60 (q, 2H), 3.32-3.28 (m 1H), 3.19-3.11 (m, 3H), 1.35 (t, 3H), 1.20 (t, 3H).

Example 16

(S)-1-(4-{1-[4-(4-chloro-phenoxy)-phenyl]-2-ethoxymethyl-1H-imidazol-4-yl}-phenoxy)-3-ethylamino-propan-2-ol dihydrochloride

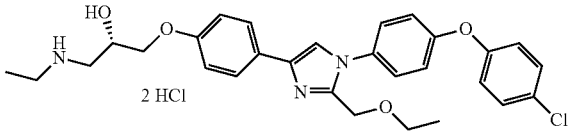 [SMILES: CCNC[C@H](O)COc1ccc(-c2cn(-c3ccc(Oc4ccc(Cl)cc4)cc3)c(COCC)n2)cc1]

A solution of 1-[4-(4-chloro-phenoxy)-phenyl]-2-ethoxymethyl-4-[4-((S)-1-oxiranylmethoxy)-phenyl]-1H-imidazole (50 mg, 0.11 mmol, from intermediate B3) in 4 mL of ethylamine in MeOH (2M) was stirred at 60° C. overnight in a teflon-capped vial. Upon completion (determined by LC/MS), the reaction was dried in vacuo and purified by silica gel flash column chromatography using a gradient of EtOAc to 4% ammonia/MeOH (2.0M) in EtOAc as an eluent to afford (S)-1-(4-{1-[4-(4-Chloro-phenoxy)-phenyl]-2-ethoxymethyl-1H-imidazol-4-yl}-phenoxy)-3-ethylamino-propan-2-ol.

The resultant free base was converted to the corresponding dihydrochloride salt by dissolution in 1 mL of DCM and 3 mL of HCl/dioxane (4.0 M) and removal of solvent in vacuo.

$^1$H-NMR (400 MHz; CD$_3$OD): δ 8.04 (s, 1H), 7.75 (d, 2H), 7.65 (d, 2H), 7.44 (d, 2H), 7.23 (d, 2H), 7.16-7.10 (m, 4H), 4.68 (s, 2H), 4.29-4.25 (m, 1H), 4.13-4.06 (m, 2H), 3.60 (q, 2H), 3.32-3.28 (m 1H), 3.19-3.11 (m, 3H), 1.35 (t, 3H), 1.20 (t, 3H).

Example Z

[3-(4-{2-butyl-1-[4-(4-chlorophenoxy)-phenyl]-1H-imidazole-4-yl}-phenoxy)-propyl]-diethyl-amine dihydrochloride

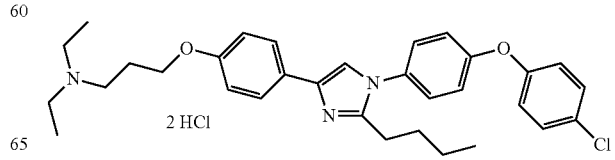

Example Z may be prepared according to the method described in PCT publication number WO 2003/075921 for Example 406.

Biological Assay

The following assay method may be used to identify compounds of Formula (I) or pharmaceutically acceptable salts thereof which are useful as inhibitors of binding of physiological RAGE ligands, such as S100b and β-amyloid, to RAGE.

S100b, β-amyloid, or CML (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 5 mM $CaCl_2/MgCl_2$) containing 1% bovine serum albumin (BSA) (300 μL/well) for 1 h at RT. The wells are aspirated.

Test compounds are dissolved in nanopure water (concentration: 10-100 μM). DMSO may be used as co-solvent. 25 μL of test compound solution in 4% DMSO is added, along with 75 μL sRAGE (6 nM FAC) to each well and samples are incubated for 1 h at 37° C. The wells are washed several times with 155 mM NaCl pH 7.2 buffer saline and are soaked for several seconds between each wash.

Non-radioactive detection is performed by adding:

10 μL Biotinylated goat F(ab')2 Anti-mouse IgG. (8.0× $10^{-4}$ mg/mL, FAC), 5 μL Alk-phos-Streptavidin (3×$10^{-3}$ mg/mL FAC), 0.42 μL per 5 mL Monoclonal antibody for sRAGE (FAC 6.0×$10^{-3}$ mg/mL) to 5 mL 50 mM imidazole buffer saline (pH 7.2) containing 0.2% bovine serum albumin and 5 mM $CaCl_2$. The mixture is incubated for 30 minutes at RT.

100 μL of complex is added to each well and incubation is allowed to proceed at rt for 1 h. Wells are washed several times with wash buffer and soaked several seconds between each wash. 100 μL 1 mg/mL (pNPP) in 1 M diethanolamine (pH adjusted to 9.8 with HCl) is added. Color is allowed to develop in the dark for 30 min to 1 h at rt. The reaction is quenched with 10 μL of stop solution (0.5-1.0 N NaOH in 50% ethanol) and the absorbance is measured spectrophotometrically with a microplate reader at 405 nm.

The Examples 1-16 (hydrochloride salt form) were tested according to the assay method described above, employing S100b or β-amyloid as the RAGE ligand, and were found to possess IC50 shown below. IC50 (μM) of in the ELISA assay represents the concentration of compound at which 50% signal has been inhibited.

| Example | IC50 (β-amyloid) (μM) | IC50 (S100b) (μM) |
|---|---|---|
| 1 | 0.85 | 0.66 |
| 2 | 0.76 | 0.55 |
| 3 | 0.80 | 0.84 |
| 4 | 0.65 | 0.54 |
| 5 | 1.02 | 0.71 |
| 6 | 0.78 | 0.77 |
| 7 | 1.17 | 1.05 |
| 8 | 1.26 | 0.80 |
| 9 | 1.59 | 1.13 |
| 10 | 1.32 | 1.14 |
| 11 | 1.02 | 0.81 |
| 12 | 1.19 | 0.98 |
| 13 | 2.16 | 4.61 |
| 14 | 2.37 | 4.56 |
| 15 | 2.47 | 3.14 |
| 16 | 1.55 | 3.13 |

Pharmacokinetics

Pharmacokinetic screening in rats was performed on various compounds to measure brain and plasma concentrations at 6 hour time point.

The parameters for the pharmacokinetic protocol were as follows.

Amount of compound: 5 mg/kg
Species: Rat; Strain: Sprague Dawley; Sex: Male
Average body weight at dose: weight ranged from 271 to 423 grams
Average age at dose: age ranged from 9 to 14 weeks
Diet Status Overnight fasting
Number of Animals (n) for each time point: 2
Dosing: Oral (PO)
Formulation: 2% Tween 80 in distilled water Each formulation was administered once by oral gavage. The dose volume was 5 mL/kg for all animals. The actual volume administered to each animal was calculated and adjusted based on the most recent body weight.

Blood samples (approximately 300 μL whole blood) at (1, 2, and 4 h) was collected from each animal via tail vein except for terminal blood samples. Terminal blood (6 h) samples were collected via cardiac puncture. All samples were collected into tubes containing lithium heparin (Multivette 600 LH-Gel, Sarstedt, Newton, N.C., USA). Following collection, the tubes were placed in refrigerator (maximum 30 minutes) or until centrifugation under refrigeration (at 2 to 8° C.) at 1500g for approximately 15 minutes. Each harvested plasma sample was then transferred into 1.2 mL polypropylene tubes, on the 96-Well Plate according to the 96-Well Plate plasma sample map and kept in freezer. Plasma samples were then analyzed for test substances.

Brain samples were collected immediately after the animals were euthanized at designated time points. Brain samples were rinsed with saline, blotted dry, and weighed. Brain samples were placed into individual containers and kept in freezer (−20° C.). Brain samples were then analyzed for test articles.

After analysis, all the plasma results are reported as ng/mL and brain sample results are reported as ng/g. In the table below, "ND" stands for not determined and "NA" stands for not applicable.

| Ex. | Brain (ng/g) | Plasma (ng/mL) | B/P Ratio | $R^1$ | $R^2$ | $Q^1$ | Config |
|---|---|---|---|---|---|---|---|
| Z | 697 | 92 | 7.7 | —$CH_3CH_2$ | —$CH_3CH_2$ | butyl | NA |
| 1 | 626 | 18 | 34.1 | —$CH_3$ | —$CH_3$ | butyl | R |
| 2 | 718 | 24 | 30.6 | —$CH_3CH_2$ | —$CH_3CH_2$ | butyl | R |
| 3 | 1120 | 48 | 23.3 | —$CH_3$ | —$CH_3$ | butyl | S |
| 4 | 610 | 74 | 8.8 | —$CH_3CH_2$ | —$CH_3CH_2$ | butyl | S |
| 5 | 3325 | 200 | 16.7 | —$CH_3$ | —$CH_3$ | ethoxymethyl | R |
| 6 | 3905 | 155 | 25.3 | —$CH_3$ | —$CH_3$ | ethoxymethyl | S |

-continued

| Ex. | Brain (ng/g) | Plasma (ng/mL) | B/P Ratio | $R^1$ | $R^2$ | $Q^1$ | Config |
|---|---|---|---|---|---|---|---|
| 7 | 1385 | 153 | 9.1 | —CH$_3$CH$_2$ | —CH$_3$ | ethoxymethyl | R |
| 8 | 2705 | 137 | 19.6 | —CH$_3$CH$_2$ | —CH$_3$ | ethoxymethyl | S |
| 9 | 537 | 76 | 7.2 | H | —CH$_3$ | butyl | R |
| 10 | 212 | 74 | 2.9 | H | —CH$_3$ | butyl | S |
| 11 | 343 | 72 | 4.8 | H | —CH$_3$CH$_2$ | butyl | R |
| 12 | 540 | 124 | 4.5 | H | —CH$_3$CH$_2$ | butyl | S |
| 13 | ND | ND | ND | H | —CH$_3$ | ethoxymethyl | R |
| 14 | ND | ND | ND | H | —CH$_3$ | ethoxymethyl | S |
| 15 | ND | ND | ND | H | —CH$_3$CH$_2$ | ethoxymethyl | R |
| 16 | ND | ND | ND | H | —CH$_3$CH$_2$ | ethoxymethyl | S |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A method for treating Alzheimer's disease comprising administering to a subject a compound of Formula (I) or a pharmaceutically acceptable salt thereof,

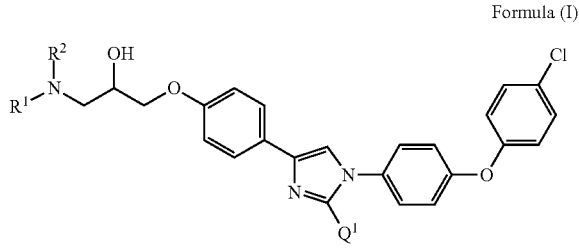

Formula (I)

wherein
$R^1$ and $R^2$ are independently selected from the group consisting of: —CH$_3$, —CH$_2$CH$_3$, —CH(CH$_3$)$_2$, and —CH$_2$CH$_2$CH$_3$; and
$Q^1$ is selected from the group consisting of —CH$_2$OCH$_2$CH$_3$ and —CH$_2$CH$_2$CH$_2$CH$_3$.

2. The method of claim 1, wherein the compound is (R)-1-(4-{2-butyl-1-[4-(4-chloro-phenoxy)-phenyl]-1H-imidazol-4-yl}-phenoxy)-3-dimethylamino-propan-2-ol or a pharmaceutically acceptable salt thereof.

3. The method of claim 1, wherein the compound is (R)-1-(4-{2-butyl-1-[4-(4-chloro-phenoxy)-phenyl]-1H-imidazol-4-yl}-phenoxy)-3-diethylamino-propan-2-ol or a pharmaceutically acceptable salt thereof.

4. The method of claim 1, wherein the compound is (S)-1-(4-{2-butyl-1-[4-(4-chloro-phenoxy)-phenyl]-1H-imidazol-4-yl}-phenoxy)-3-dimethylamino-propan-2-ol or a pharmaceutically acceptable salt thereof.

5. The method of claim 1, wherein the compound is (S)-1-(4-{2-butyl-1-[4-(4-chloro-phenoxy)-phenyl]-1H-imidazol-4-yl}-phenoxy)-3-diethylamino-propan-2-ol or a pharmaceutically acceptable salt thereof.

6. The method of claim 1, wherein the compound is (R)-1-(4-{1-[4-(4-chloro-phenoxy)-phenyl]-2-ethoxymethyl-1H-imidazol-4-yl}-phenoxy)-3-dimethylamino-propan-2-ol or a pharmaceutically acceptable salt thereof.

7. The method of claim 1, wherein the compound is (S)-1-(4-{1-[4-(4-chloro-phenoxy)-phenyl]-2-ethoxymethyl-1H-imidazol-4-yl}-phenoxy)-3-dimethylamino-propan-2-ol or a pharmaceutically acceptable salt thereof.

8. The method of claim 1, wherein the compound is (R)-1-(4-{1-[4-(4-chloro-phenoxy)-phenyl]-2-ethoxymethyl-1H-imidazol-4-yl}-phenoxy)-3-diethylamino-propan-2-ol or a pharmaceutically acceptable salt thereof.

9. The method of claim 1, wherein the compound is (S)-1-(4-{1-[4-(4-chloro-phenoxy)-phenyl]-2-ethoxymethyl-1H-imidazol-4-yl}-phenoxy)-3-diethylamino-propan-2-ol or a pharmaceutically acceptable salt thereof.

* * * * *